United States Patent
Kane et al.

(10) Patent No.: US 10,814,036 B2
(45) Date of Patent: Oct. 27, 2020

(54) DRUG-ELUTING LIVE TISSUE FOR TRANSPLANTATION

(71) Applicant: BAYLOR UNIVERSITY, Waco, TX (US)

(72) Inventors: Bob Kane, Waco, TX (US); Babatope Akinbobuyi, Waco, TX (US); Charles Chang, Waco, TX (US); Bashoo Naziruddin, Waco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

(21) Appl. No.: 15/805,412

(22) Filed: Nov. 7, 2017

(65) Prior Publication Data

US 2018/0177918 A1   Jun. 28, 2018

Related U.S. Application Data

(60) Provisional application No. 62/418,455, filed on Nov. 7, 2016.

(51) Int. Cl.

| | |
|---|---|
| *A61L 27/36* | (2006.01) |
| *C12N 5/071* | (2010.01) |
| *A61L 27/38* | (2006.01) |
| *A61L 27/54* | (2006.01) |
| *A61K 31/18* | (2006.01) |

(Continued)

(52) U.S. Cl.
CPC .......... *A61L 27/3683* (2013.01); *A61K 31/18* (2013.01); *A61K 31/216* (2013.01); *A61K 47/54* (2017.08); *A61K 47/545* (2017.08); *A61K 47/555* (2017.08); *A61L 27/3687* (2013.01); *A61L 27/3695* (2013.01); *A61L 27/3839* (2013.01); *A61L 27/54* (2013.01); *A61P 29/00* (2018.01); *A61P 37/06* (2018.01); *C12N 5/0006* (2013.01); *C12N 5/0676* (2013.01); *A61L 2300/41* (2013.01); *A61L 2300/418* (2013.01);

(Continued)

(58) Field of Classification Search
CPC ...... A61K 47/54; A61K 47/555; A61K 31/18; A61K 47/545; A61K 31/216; A61L 27/3683; A61L 27/3839; A61L 27/54; C12N 5/0676; A61P 37/06; A61P 29/00
See application file for complete search history.

(56) References Cited

U.S. PATENT DOCUMENTS

| | | |
|---|---|---|
| 5,821,343 A | 10/1998 | Keogh |
| 5,977,252 A | 11/1999 | Wagner et al. |

(Continued)

FOREIGN PATENT DOCUMENTS

| | | |
|---|---|---|
| EP | 0 732 110 | 9/1996 |
| WO | 02/00685 | 1/2002 |

OTHER PUBLICATIONS

Stabler et al. Surface Re-engineering of Pancreatic Islets with Recombinant azido-Thrombomodulin. Bioconjugate Chem. 2007, 18, 1713-1715, p. 1713-1715. (Year: 2007).*

(Continued)

*Primary Examiner* — Sean C. Barron
(74) *Attorney, Agent, or Firm* — Jackson Walker LLP

(57) ABSTRACT

Methods for the ex vivo modification of the surfaces of viable tissue result in tissue modifications that are stable and/or result in the controlled release of active compounds, and are expected to provide effective protection for transplanted tissue subsequent to transplant.

11 Claims, 32 Drawing Sheets

(51) Int. Cl.
  A61K 47/54     (2017.01)
  A61P 37/06     (2006.01)
  A61P 29/00     (2006.01)
  A61K 31/216    (2006.01)
  C12N 5/00      (2006.01)
(52) U.S. Cl.
  CPC ..... A61L 2300/426 (2013.01); A61L 2400/16
                                              (2013.01)

(56) References Cited

U.S. PATENT DOCUMENTS

| | | | |
|---|---|---|---|
| 6,570,040 | B2 | 5/2003 | Saxon et al. |
| 6,861,211 | B2 | 3/2005 | Levy et al. |
| 7,067,272 | B2 | 6/2006 | Nemori et al. |
| 7,998,925 | B2 | 8/2011 | Kane et al. |
| 8,658,348 | B2 | 2/2014 | Kane et al. |
| 2005/0176093 | A1 | 8/2005 | Ahn et al. |
| 2015/0174268 | A1* | 6/2015 | Li ............ A61K 47/6855 424/178.1 |

OTHER PUBLICATIONS

Bruni et al. Islet cell transplantation for the treatment of type 1 diabetes: recent advances and future challenges. Diabetes, Metabolic Syndrome and Obesity: Targets and Therapy 2014:7 211-223. (Year: 2014).*
Zhang et al. Bio-Inspired Liposomal Thrombomodulin Conjugate through Bio-Orthogonal Chemistry. Bioconjugate Chem 2013, 24, 530-599. (Year: 2013).*
Song et al. Toll-like receptor 4 on islet β cells senses expression changes in high-mobility group box 1 and contributes to the initiation of type 1 diabetes. Experimental and Molecular Medicine, vol. 44, No. 4, 260-267, Apr. 2012. (Year: 2012).*
W. Reusch. Chemistry of Amines, 9 page web article (May 2013). (Year: 2013).*
Santi et al. Predictable and tunable half-life extension of therapeutic agents by controlled chemical release from macromolecular conjugates. PNAS (2012), v109(16), 6211-6216 and 8 page supplement. (Year: 2012).*
Yamada et al. Discovery of Novel and Potent Small-Molecule Inhibitors of NO and Cytokine Production as Antisepsis Agents: Synthesis and Biological Activity of Alkyl 6-(N-Substituted sulfamoyl)cyclohex-1-ene-1-carboxylate. Journal of Medicinal Chemistry (2005), 48, 7457-7467 (Year: 2005).*
Kane, et al., "Drug Delivery by Transplanted Islets", Baylor University, 2017, retrieved from: http://abstracts.biomaterials.org/data/papers/2017/abstracts/0544.pdf, 1 page.
Chang, et al., "The Role of Toll-Like Receptor 4 in Islet Transplantation and a Novel Method of Protection Using Chemical Surface Modification", 2017 American Transplant Congress Meeting, Apr. 29, 2017, retrieved from: https://https://atcmeetingabstracts.com/abstract/the-role-of-toll-like-receptor-4-in-islet-transplantation-and-a-novel-method-of-protection-using-chemical-surface-modification/ 6 pages.
SoRelle, et al., "Comparison of surface modification chemistries in mouse, porcine, and human islets", Society for Biomaterials, Wiley Periodicals, Published online May 24, 2014, 9 pages.
Gao, et al., "TLR4 Mediates Early Graft Failure After Intraportal Islet Transplantation", American Journal of Transplantation, 2010, 10 pages.
Ro, et al., "Roles of Toll-Like Receptors in Allogeneic Islet Transplantation", Transplantation Journal, vol. 94, No. 10, Nov. 27, 2012, 8 pages.
Vivot, et al., "Pro-Inflammatory and Pro-Oxidant Status of Pancreatic Islet In Vitro is Controlled by TLR-4 and HO-1 Pathways", PLOS One, Oct. 14, vol. 9, Issue 10, 10 pages.
Wang et al., "COMP-Ang1 promotes long-term survival of allogeneic islet grafts in a bioinert perforated chamber by inhibiting inflammation via inhibition of the TLR4 signaling pathway", Biotechnol Lett (2016), 38: pp. 1033-1042.
Dong, et al., "Cell-Permeable Peptide Blocks TLR4 Signaling and Improves Islet Allograft Survival", Cell Transplantation, 2016, vol. 25, pp. 1319-1329.
Howell, et al., "Role of Toll-Like Receptors in Liver Transplantation", Liver Transplantation, 2014, vol. 20, pp. 270-280.
Shao, et al., "TAK-242 treatment ameliorates liver ischemia/reperfusion injury by inhibiting TLR4 signaling pathway in a swine model of Maastricht-category-III cardiac death", Biomedicine & Pharmacotherapy, 2016, vol. 84, pp. 495-501.
Santi, et al., "Predictable and tunable half-life extension of therapeutic agents by controlled chemical release from macromolecular conjugates", PNAS, Apr. 17, 2012, vol. 109, No. 16, pp. 6211-6216.
Chang, et al., "Copper-free click chemistry in living animals", PNAS, Feb. 2, 2010, vol. 107, No. 5, pp. 1821-1826.
Thirumurugan, et al., "Click Chemistry for Drug Development and Diverse Chemical—Biology Applications", Chemical Reviews, 2013, vol. 113, pp. 4905-4979.
Huang, et al. "Synthesis and evaluation of N-acyl sulfonamides as potential prodrugs of cyclin-dependent kinase inhibitor JNJ-7706621", Bioorganic & Medicinal Chemistry Letters, 2006, vol. 16, pp. 3639-3641.
Iley, et al., "Kinetics and mechanism of hydrolysis of N-amidomethylsulfon-amides", The Royal Society of Chemistry, 2001, pp. 749-753.
Larsen, et al., "Prodrug forms for the sulfonamide group-IV. Kinetics of hydrolysis of N-sulfonyl pseudourea derivatives", Acta Pharm. Nordica, 1989, vol. 1, pp. 31-40.
Ashley, et al., "Hydrogel drug delivery system with predictable and tunable drug release and degradation rates", PNAS, Feb. 5, 2013, vol. 110, No. 6, pp. 2318-2323.
De La Fuente, et al., "Biotinylation of membrane proteins accessible via pulmonary circulation in normal and hyperoxic rats", American Journal of Physiology, Mar. 1997, vol. 272, No. 3, part 1, pp. L461-L470.
Halfter, W. "Anterograde tracing of retinal axons in the avian embryo with low molecular weight derivatives of biotin", Developmental Biology, Feb. 1987, 14 pages.
Hoya, et al., "A Novel Intravascular Drug Delivery Method Using Endothelial Biotinylation and Avidin-Biotin Binding", Drug Delivery, Oct.-Dec. 2001, vol. 8, No. 4, 8 pages.
Hoffmann-Fezer, et al., "Direct in vivo biotinylation of erythrocytes as an assay for red cell survival studies", Annals of Hematology, 1991, vol. 63, No. 4, pp. 214-217.
De Bank, et al. "Surface Engineering of Living Myoblasts via Selective Periodate Oxidation", Biotechnology and Bioengineering-Combinatorial Chemistry, Mar. 30, 2003, vol. 81, No. 7, pp. 800-808.
McFetridge, et al., "Preparation of Porcine Cartoid Arteries for Vascular Tissue Engineering Applications", Journal of Biomedical Materials Research Part A, vol. 70A, Issue 2, pp. 224-234, (Jun. 2004).
Hermanson, G., "Bioconjugate Techniques", Academic Press, pp. 19-21 and 114-116, (1996).
Fabris, et al., "Labeling of Platelet Surface Glycoproteins with Biotin Derivatives", Thrombosis Research, May 15, 1992, pp. 409-419.
Bayer, et al., "Biocytin Hydrazide—A Selective Label for Sialic Acids, Galactose and Other Sugars in Glycoconjugates Using Avidin-Biotin Technology", Analytical Biochemistry, 1988, vol. 170, No. 2, pp. 271-281.
Rando, et al., "Labeling of Oxidized Cell Surface Membranes by Acyl Hydrzides", Biochimica et Biophysica Acta, 1979, vol. 557, No. 2, pp. 354-362.
Huestis, W.H., "Preliminary Characterization of the Acetylcholine Receptor in Human Erythrocytes", Journal of Supramolecular and Cellular Biochemistry, 1976, vol. 4, No. 3, pp. 355-365.
Karlin, et al., "The Affinity Labeling of Partially Purified Acetylcholine Receptor from Electric Tissue of Electrophorus", Proceed-

(56) References Cited

OTHER PUBLICATIONS ing of the National Academy of Sciences of the United States of America, 1973, vol. 70, No. 12, 5 pages.

Burns, J., et al., "Selective Reduction of Disulfides by Tris(2-carboxyethyl) phosphine" Journal of Organic Chemistry, American Chemical Society, 1991, vol. 56, No. 8, pp. 2648-2650.

International Preliminary Report on Patentability issued by the European Patent Office dated Apr. 3, 2007 for International Application No. PCT/US2005/034991, 12 Pages.

International Search Report issued by the European Patent Office dated Mar. 9, 2007 for International Application No. PCT/US2005/034991, 7 Pages.

Communication Pursuant to Article 94(3) EPC issued by the European Patent Office dated Dec. 10, 2010 for International Application No. PCT/US2005/034991, 5 Pages.

\* cited by examiner

FIG. 7
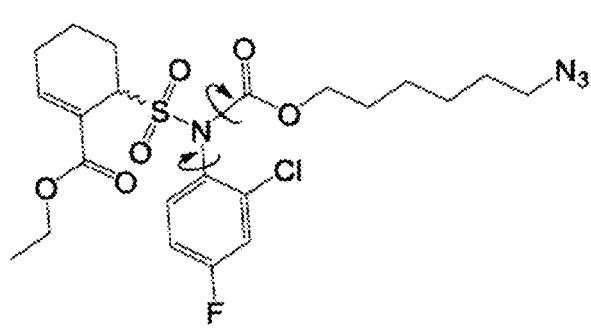
44
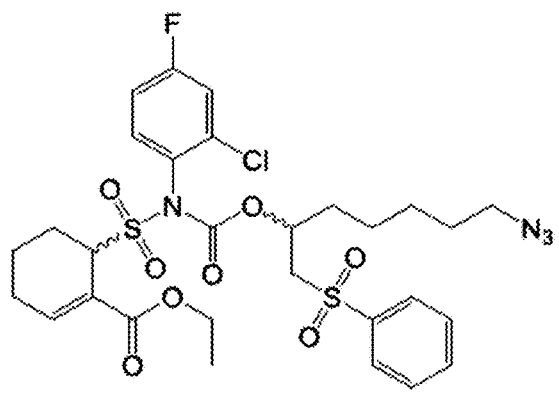
45

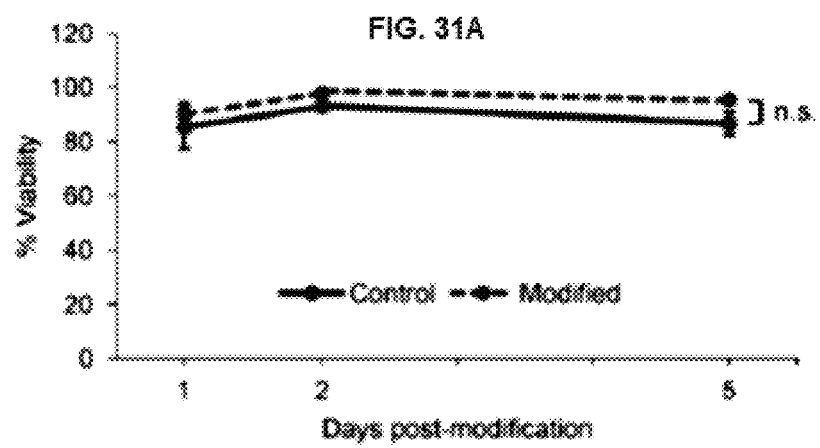
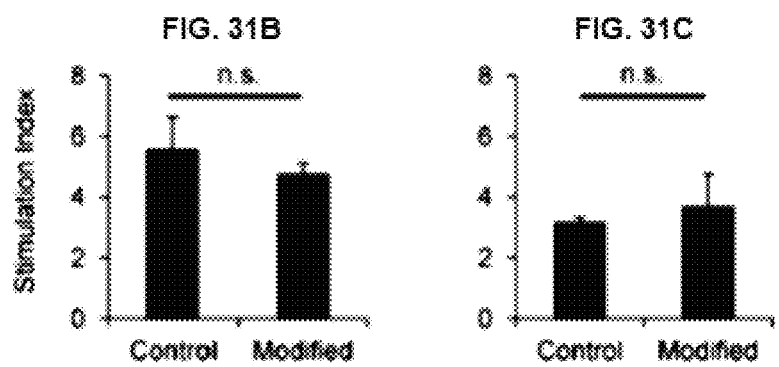
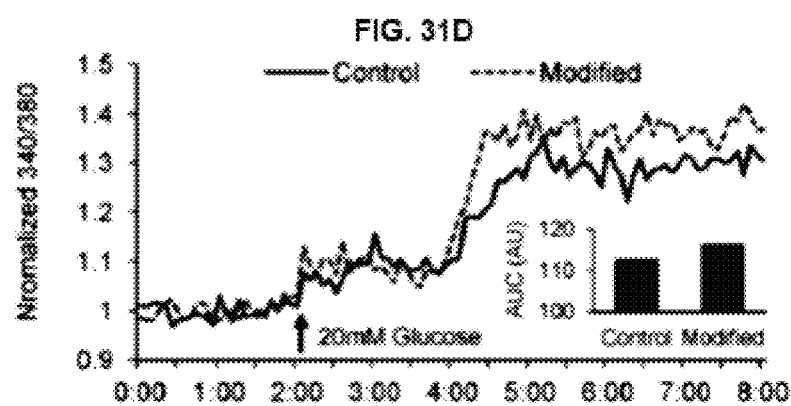

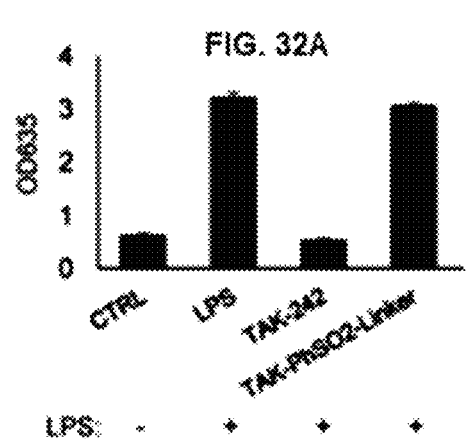
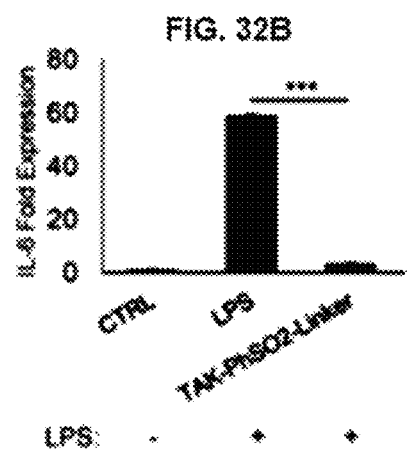
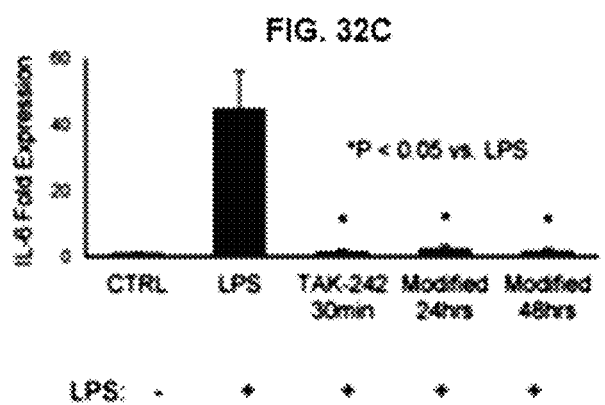
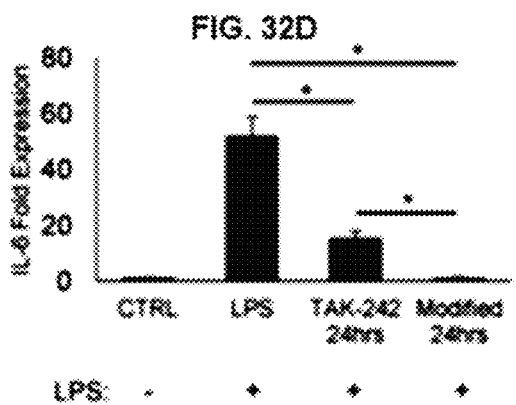
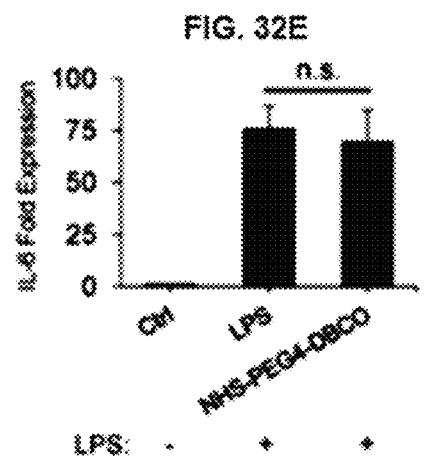

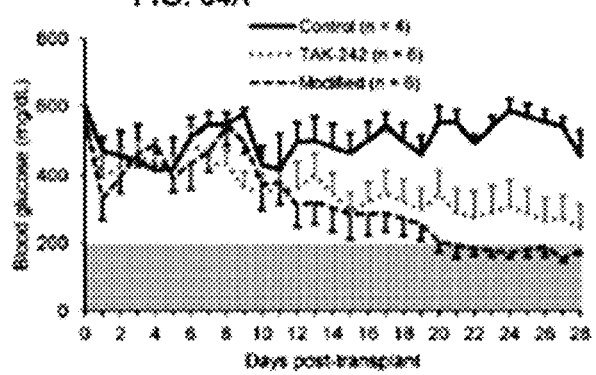
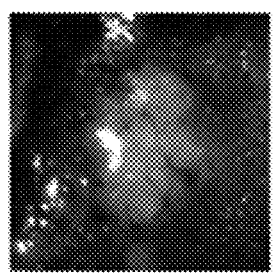
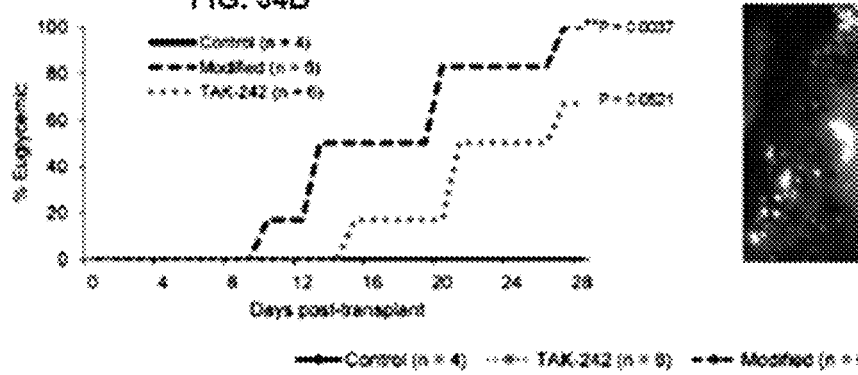
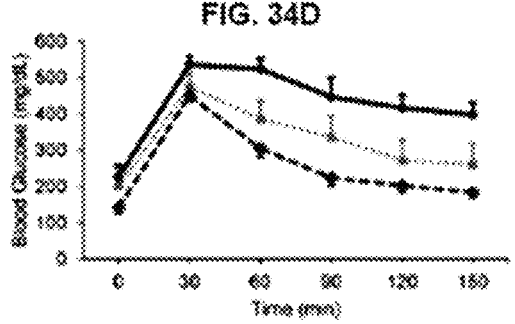
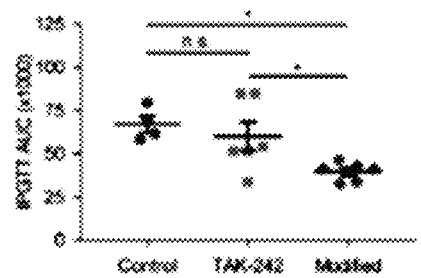

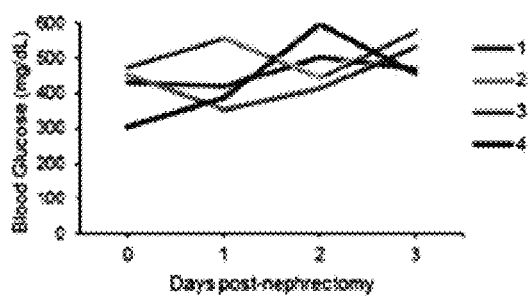
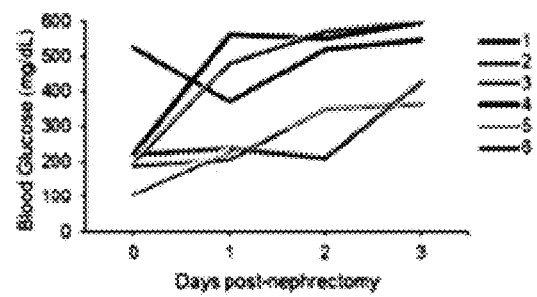
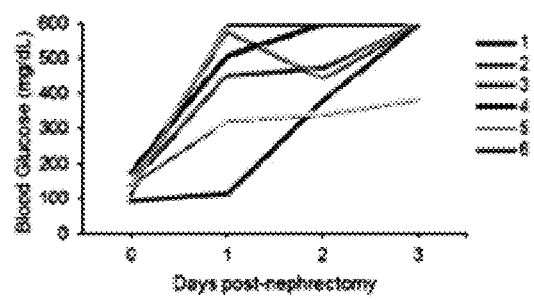

DRUG-ELUTING LIVE TISSUE FOR TRANSPLANTATION

This application claims priority to U.S. Provisional Patent Application No. 62/418,455, filed Nov. 7, 2016, entitled "Drug-Eluting Live Tissue for Transplantation," the entire contents of which are hereby incorporated by reference.

BACKGROUND

The present disclosure relates to methods involving drug-eluting live tissue for maximization of transplantation success.

Tissue transplantation involves moving tissue from one body to another, or from a donor site to another location on the same body, to replace damaged or absent tissue. Transplanting tissue between different bodies is called allogenic transplantation. Transplanting tissue within a single body is called autologous transplantation. Both autologous and especially allogenic transplants often encounter problems with transplant rejection, in which the recipient body has an adverse response to the transplanted tissue, which may lead to failure of the transplant and the need for removal. A variety of therapeutic drugs are often administered to the recipient in conjunction with an autologous or allogenic transplant in order to reduce the adverse responses and improve the potential for survival of the transplant. These drugs may include immunosuppressants, anti-inflammatories, and clotting inhibitors, amongst others. However, these drugs are typically administered systemically in bolus and are non-selective in action, often resulting in damage to tissues throughout the body.

Spatially or temporally controlled drug delivery in order to control the release of active compounds is promising for localized delivery of drugs. Significant advantages associated with drug localization are widely accepted, as exemplified by successful approaches as varied as topical creams, implanted biomaterials, and antibody-drug conjugates. Antibody-drug conjugates (ADCs) are one popular example of an attempt to spatially control drug delivery. Drug-coated and drug-eluting stents are also utilized in medical applications. Drug-eluting stents provide a slow release of active drug localized at the site where it is needed, boosting the local dose while minimizing the off-target exposure. While small-molecule therapeutics can be used in order to increase the survival of transplanted tissue, often these potent drugs exhibit prohibitive side-effect profiles when utilized systemically. Techniques for localized delivery of drugs in transplantation have not been fully explored or employed.

An archetypal model for transplantation is the transplantation of pancreatic islets of Langerhans for the treatment of brittle diabetes as a result of type 1 or type 3c diabetes mellitus. Brittle diabetes is characterized by significantly impaired or nonexistent insulin production, problematic hypoglycemic unawareness, severe hypoglycemic events, and glycemic lability. While most diabetics successfully manage their diabetes with a multiple daily insulin injection regimen or insulin pumps, the subpopulation of patients who fail to respond to existing insulin therapies and account for a significant proportion of diabetes-related morbidity and mortality have been shown to respond well to islet transplantation.

In islet transplantation, acute inflammation during the peritransplant period can result in the loss of 50% to 70% of the transplanted islets and contribute to poor transplant outcomes including the need for multiple donor pancreases to achieve insulin independence. The early islet damage is mediated by sterile inflammation mechanisms such as innate immunity, ischemia/reperfusion injury (IRI), and hypoxia. Several methods to protect islet grafts from inflammatory damage and other insults have been proposed, including treatment with anti-inflammatory agents, co-transplant with mesenchymal stem cells, encapsulation, and islet surface modification.

This acute graft injury is not a problem only in islet transplantation, but manifests itself as primary graft dysfunction in lung, liver, heart, kidney, and pancreas transplantation, occurring in a significant proportion (~20% to 30%) of organ transplants. There is a growing recognition of the significance of toll-like receptors (TLRs) as potential targets for limiting inflammation and improving transplantation outcomes. Specifically, toll-like receptor 4 (TLR4) has been identified as a major mediator of graft inflammation and dysfunction after organ transplantation, making it a logical target for alleviating graft injury posttransplant.

SUMMARY

The present disclosure pertains to methods for covalent linkage of protective compounds to live tissue, and particularly to the covalent linkage of immunsuppressant, anti-inflammatory, and anti-clotting drugs to live tissue for transplantation.

The present disclosure utilizes chemistry developed for the ex vivo modification of the surfaces of viable tissue. The modifications are stable and/or result in the controlled release of active compounds, and are expected to provide effective protection for transplanted tissue subsequent to transplant. The methods and techniques described herein involve the synthesis of active conjugatible compounds and the development of various bioconjugation approaches for modifying live tissue.

It is possible to covalently modify cell surfaces without reducing cell viability, initiating stress responses, or interfering with cellular signaling. A variety of cell types have been successfully surface-modified, including erythrocytes, T-cells and B-cells, cancer cells, leukocytes, and macrophages. Cell-surface modification has been accomplished using a variety of chemistries. While the modification of surface amines with isocynates and active esters has been the most common approach, other simple chemical modification methods have also been utilized including the condensation of reactive amines with cell-surface carbonyls introduced by periodate oxidation and the alkylation of free thiols introduced by reduction of the cell-surface disulfides. The association of catechols with cell surfaces, and the use of enzymes including biotin ligase or transglutaminase or sortase, are additional strategies used to modify cell surfaces, demonstrating the wide range of biocompatible chemistries available. Adding to the repertoire of modification tools, several of the recent reports of cell-surface modification have involved a two-step procedure, whereby a simple linker molecule is initially attached to the cell surface, followed by further functionalization of the linker via a "click" reaction. "Click" chemistry describes a number of chemical condensation reactions that have been shown to be exceptionally efficient, biorthogonal, and biocompatible. These reactions have been extensively utilized in bioconjugation chemistry, including in situ reactions in living mammals.

Less attention has been paid to the covalent modification of bulk living tissue. The present disclosure demonstrates that covalent modification of bulk tissue is possible using simple reactions, where the modifications are durable and stable in serum. Different tissue types have demonstrated different reactivities. FIG. 1 shows the results of covalent biotinylation of fresh bulk tissues with chemiluminescence (SA-HRP) detection. The stars designate control unreacted tissue. FIG. 1A shows fetal pig skin oxidized with sodium periodate and labeled with biotin-hydrazide. FIG. 1B shows bovine meniscus modified with biotin-NHS ester. FIG. 1C shows bovine pericardium reduced using different concentrations of TCEP and labeled using biotin-maleimide.

The present disclosure relates to methods for covalent linkage of potent protective compounds to the surface of tissue prior to transplantation utilizing appropriate chemical approaches and carefully selected linkers. This leads to localized and sustained release of the compounds at the transplantation site. This ex vivo modification of tissue with active drugs including immunsuppressant, anti-inflammatory, and anti-clotting agents limits the treatment to the local microenvironment and boosts the effective dose while minimizing off-target exposure and limiting rejection. The present methods allow the active drug to be released at a tailored rate, thereby promoting a localized protected environment. The methods have been shown to promote successful tissue transplantation, specifically pancreatic islet cell transplantation. The methods are applicable to a wide variety of types of tissue and organ transplantation, including especially liver, kidney, or lung transplants.

The present methods have been demonstrated to maintain cell viability and cellular signaling, and to limit stress responses following transplantation. By attaching bioactive compounds to live tissue in a manner that is biocompatible and that allows the release of the active component at a tailored rate, the transplanted tissue can create a localized protective environment. The local environment can be maintained post-transplantation for an extended period of time that is dependent on the release kinetics of the bioactive compound. A variety of drugs, including but not limited to immunsuppressant, anti-inflammatory, and anti-clotting agents, with a strong record for clinical safety and efficacy can be used in this system depending on stability and kinetic characteristics.

The systemic administration of immunosuppressive and anti-inflammatory drugs is routinely employed in transplantation in order to minimize graft rejection and improve graft survival. Localized drug delivery has the potential to improve transplant outcomes by providing sustained exposure to efficacious drug concentrations while avoiding systemic immunosuppression and other dose-limiting off-target side effects. Preferred embodiments of the present disclosure include a novel prodrug and its direct covalent conjugation to pancreatic islets via a cleavable linker. Post-transplant, slow linker hydrolysis results in the extended release of a potent anti-inflammatory antagonist of toll-like receptor 4 (TLR4), localized to the site of implantation. This covalent islet modification is accomplished under physiologically compatible conditions, and the drug-eluting islets significantly reduce the time and the minimal effective dose of islets necessary to achieve normoglycemia in a murine transplantation model. This direct prodrug modification of islets is well tolerated and preserves their functionality while affording significantly superior transplant outcomes.

BRIEF DESCRIPTION OF DRAWINGS

FIG. 7 depicts potential isomers for compounds 44 and 45.

FIG. 31A shows viability of control and modified islets assessed by staining postmodification.

FIG. 31B shows stimulation index of control and modified islets 24 h postmodification.

FIG. 31C shows stimulation index of control and modified islets 72 h postmodification.

FIG. 31D shows intracellular Ca2+ flux assessment by fura-2AM staining.

FIG. 32A shows assessment of inhibition of TLR4-mediated NFkB upregulation for free TAK-242 and the TAK-PhSO$_2$-Linker prodrug using a colorimetric assay.

FIG. 32B shows assessment of islets covalently modified with TAK-PhSO$_2$-Linker protected from LPS challenge as determined by IL-6 expression.

FIG. 32C shows assessment of protection of modified islets was out to 48 h postmodification.

FIG. 32D shows assessment of protection from TLR4-mediated inflammation 24 hours post treatment for both free TAK-242 and the covalent TAK-PhSO$_2$-Linker.

FIG. 32E shows assessment of protection of islet surfaces functionalized with NHS-PEG4-DBCO.

FIG. 34A shows mean nonfasting blood glucose in control, TAK-242, and modified groups of mice.

FIG. 34B shows mice achieving euglycemia in all groups.

FIG. 34C shows a dissecting microscopic image of a neovascularized islet graft from a mouse that received 100 modified islets.

FIG. 34D shows IPGTT data, blood glucose over time, from mice on day 30 posttransplant.

FIG. 34E shows IPGTT data (AUC×1000) from mice on day 30 posttransplant.

FIG. 35A shows blood glucose of mice after islet graft removal for control group mice.

FIG. 35B shows blood glucose of mice after islet graft removal for TAK-242 group mice.

FIG. 35C shows blood glucose of mice after islet graft removal for modified group mice.

DETAILED DESCRIPTION OF PREFERRED EMBODIMENTS

Figure 1A:
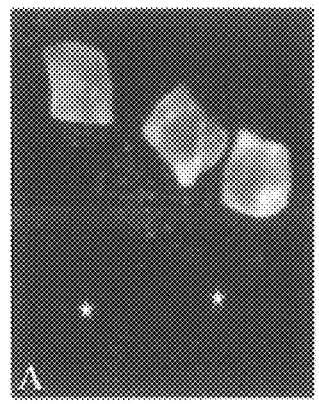
FIG. 1A shows results of covalent biotinylation of fresh bulk tissues with chemiluminescence (SA-HRP) detection, where the stars designate control unreacted tissue, namely, fetal pig skin oxidized with sodium periodate and labeled with biotin-hydrazide.
Figure 1B:
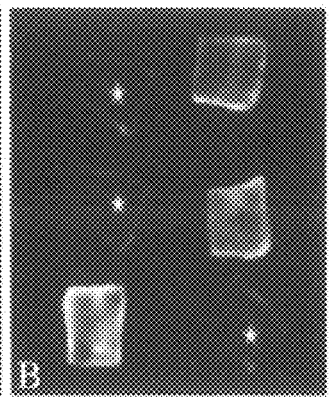
FIG. 1B shows bovine meniscus modified with biotin-NHS ester.
Figure 1C:
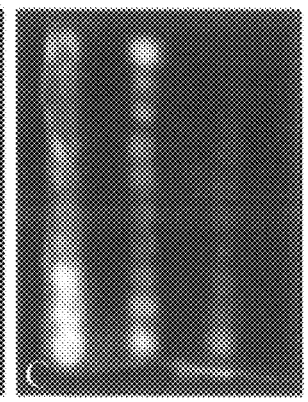
FIG. 1C shows bovine pericardium reduced using different concentrations of TCEP and labeled using biotin-maleimide.

The present disclosure relates to the preparation of live tissue that releases protective drugs after transplantation. A preferred embodiment of this method involves the covalent linkage of modified drugs to live tissue prior to transplantation. Preferred embodiments of the methods relate to covalent linking of bioactive compounds to live cells in a manner that is biocompatible and allows for slow-release of the active compound to promote successful organ transplantation.

Preferred embodiments of the present method include surface modification of the tissue to be transplanted. Additional preferred embodiments include modification of the immunosuppressive or anti-inflammatory drug to allow for its attachment to the tissue surface by a releasable linker.

Preferred embodiments described herein include a living tissue chemical modification strategy which affords drug-eluting islets that slowly release a potent anti-inflammatory TLR4-antagonist. This covalent modification significantly reduces the islet mass and time needed to achieve euglycemia in a streptozotocin-induced diabetic mouse model. In C57BL/6 mice, having a robust inflammatory foreign body response, the syngeneic transplant model was used to study the anti-inflammatory effects of the released drug on the innate inflammatory response, independent of adaptive immunity. Results demonstrate that the chemical modification of islet surfaces with releasable prodrugs has the potential for superior localized drug efficacy resulting in improved transplant outcomes.

Additional preferred embodiments described herein relate to the ex vivo modification of live tissue surface with a cleavable TLR4-antagonist prodrug. The locally released drug provides sustained protection to islets against TLR4-mediated inflammation, and the use of these 'drug-eluting transplants' provides significantly improved outcomes in islet transplantation.

The role of TLRs in innate antipathogenic immunity is widely known. Recently, TLR4 has been demonstrated to play a major role in sterile inflammation, acute graft dysfunction and allograft rejection, and autoimmune disease. Studies involving anti-TLR4 antibodies, siRNA, and TLR4−/− animals have shown significant therapeutic benefits against acute injury mediated by inflammatory DAMPs. TAK-242 is a selective TLR4-antagonist that was initially developed and clinically evaluated for the treatment of sepsis. The protective effects of TAK-242 against TLR4-mediated inflammation have been previously demonstrated in models of neural stress, liver IRI, and even autoimmune disease.

Preferred embodiments utilize TAK-242 for blocking TLR4-mediated inflammation in islets in vitro. TAK-242 significantly blocked LPS-mediated inflammation in islets as demonstrated by gene and cytokine analysis. LPS stimulation of islets significantly upregulated both CXCL10 and CCL2, both known to have a significant negative effect on islet transplantation outcomes but this inflammation was largely inhibited by TAK-242 treatment. Cytokine profile analysis from LPS-challenged islets revealed that in addition to CXCL10 and CCL2, the acute inflammatory cytokines IL-6 and TNF-α were upregulated, as was the myeloid cell chemoattractant CXCL10.

Preferred embodiments herein include TAK-PhSO$_2$-Linker, a conjugatable, slow-release prodrug form of TAK-242, which can be readily covalently linked to surface-functionalized tissues, and which can elute TAK-242 via β-elimination at a tunable rate. The structure of TAK-PhSO$_2$-Linker is shown below:

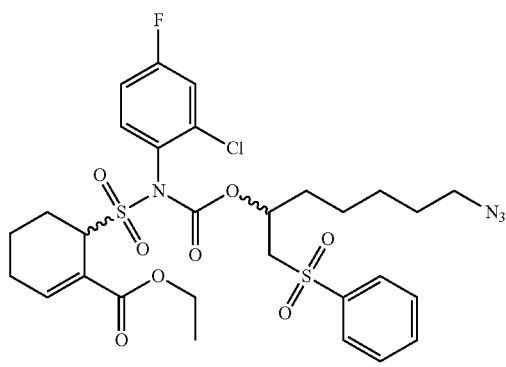 [SMILES: CCOC(=O)C1=CCCCC1S(=O)(=O)N(C(=O)OC(CCCCCN=[N+]=[N-])CS(=O)(=O)c1ccccc1)c1ccc(F)cc1Cl]

Analysis of cleavage kinetics revealed that free TAK-242 is released from the prodrug with a half-life of approximately 25 h. In preliminary islet modification experiments, the surface labeling of murine islets with a fluorophore using a 'Click' chemistry approach was demonstrated. A competitive binding assay demonstrates that the TAK-PhSO$_2$-Linker prodrug can be conjugated to islets.

Importantly, this conjugation chemistry can be applied to other tissues and organs, so this 'drug-eluting transplant' strategy has broad applicability. Viability and functionality assays in vitro have revealed the safety profile and tolerability of islets to this conjugation chemistry. The modified islets exhibit lasting protection against TLR4-mediated inflammation in vitro. At 24 and 48 h post-modification, modified islets still demonstrated essentially complete inhibition of LPS-mediated inflammation. On the other hand, TAK-242 is able to completely inhibit LPS-mediated inflammation immediately after treatment, but beings to lose its effectiveness by 24 h.

Data clearly support the advantage of chemically modified drug-eluting islets. Transplant data here show that the translation of this chemistry into the clinic will substantially reduce the dose of islets needed to achieve insulin independence and facilitate single-donor transplant success. The ex vivo modification of tissues can be easily implemented during organ procurement or prior to transplant by normothermic machine perfusion in vascularized organs, which is increasingly common, or by directly washing tissues and cells in modification buffers. Clinical implementation in the field of transplantation will provide a significant advantage in minimizing primary graft dysfunction and improving longterm outcomes.

Certain preferred embodiments of the present invention utilize sulfonamide drugs such as TAK-242, a potent TLR4 antagonist. TAK-242 is a simple sulfonamide that is an extremely active inhibitor of TLR4 activation, has demonstrated an excellent safety profile in clinical trials, and has been shown to mediate the production of inflammatory cytokines in a variety of contexts, including ischemia/reperfusion injuries. The formulation of sulfonamide drugs as prodrugs has been explored extensively, and N-acyl sulfonamides have been described as exceptional prodrug candidates. Studies indicate that simple N-acyl sulfonamides are stable towards esterase activity, which allows the use of a "tunable" β-elimination linker strategy in preferred embodiments.

Figure 3:
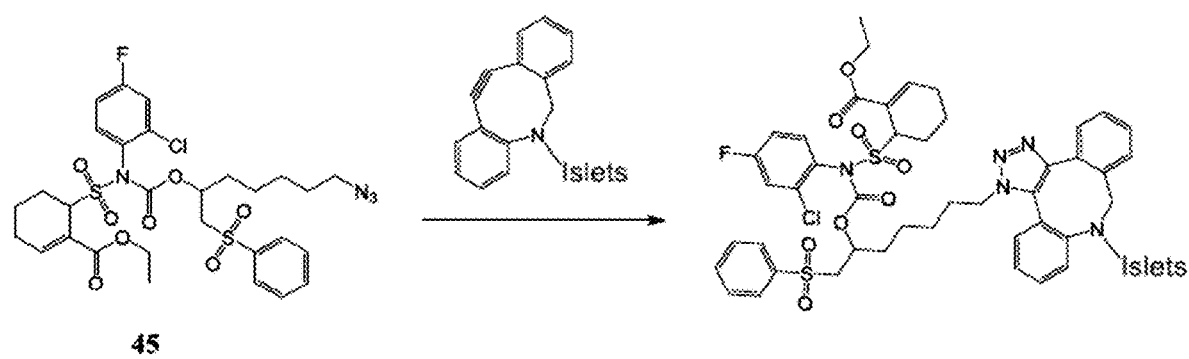
FIG. 3 shows an exemplary scheme for the conjugation of TAK-242 to islets via "click" chemistry and a releasable linker.

Several potent TLR4 antagonists have been described in the literature, including lipid A mimetics CRX-526, E5564, and FP7, as well as the arylsulfonamide TAK-242 (see FIG. 3). TAK-242 has potent TLR4 inhibition (IC50 values of 1 to 30 nM) in both human and murine models and a clinical safety profile that has been demonstrated in human clinical trials. TAK-242 has been shown to function by covalently binding to Cys747 in the intracellular TIR domain of TLR4 and inhibiting the adapter proteins TIRAP and TRAM from associating with the receptor, thereby inhibiting the inflammatory MyD88-NFkB axis. The sulfonamide motif in TAK-242 offers a potential reactive group for chemical modification into a covalently-linked prodrug.

Additional preferred embodiments utilize thrombin inhibitor drugs such as dabigatran. Dabigatran is a potent and reversible FDA approved small-molecular inhibitor of thrombin. Dabigatran is ideal for use in the present methods, as it is used clinically as an orally-dosed "double prodrug" dabigatran etexilate, which has ester and carbamate functionalities that are cleaved by esterases, revealing the active drug. The present methods take advantage of the same functional group handles in order to immobilize the drug on the tissue surface, using the same "tunable" chemical hydrolysis linker chemistry.

Additional embodiments utilize any suitable drugs expected to protect transplanted tissues. For example, drugs can be selected from the broad categories of anti-oxidants (deferiprone, deferisirox), anti-inflammatories (Withaferin), and immunosuppressants (tacrolimus, rapamycin). The same mechanisms for attachment and release can be utilized for these drugs.

Additional preferred embodiments use "tunable" carbamates for attachment of the drug to the tissue and eventual release of the drug. This approach utilizes the β-elimination of an amine from a carbamate, utilizing prosthetic groups to tune the pK of the proton removed in the elimination reaction, and providing half-lives ranging from 14 hours to 100 days. This application facilitates the use of "click" chemistry, allowing for adaptation of the method for various applications involving tissue surface modification.

In a preferred embodiment, carbamates are used for modification of the immunosuppressive drug and attachment to the tissue surface. The sulfonamide drug TAK-242 may be attached to the linker alcohol (7-azido-1-(phenylsulfonyl) heptan-2-ol) via the carbamate moiety, generating a molecule which slowly releases the active drug in vivo.

Figure 2:
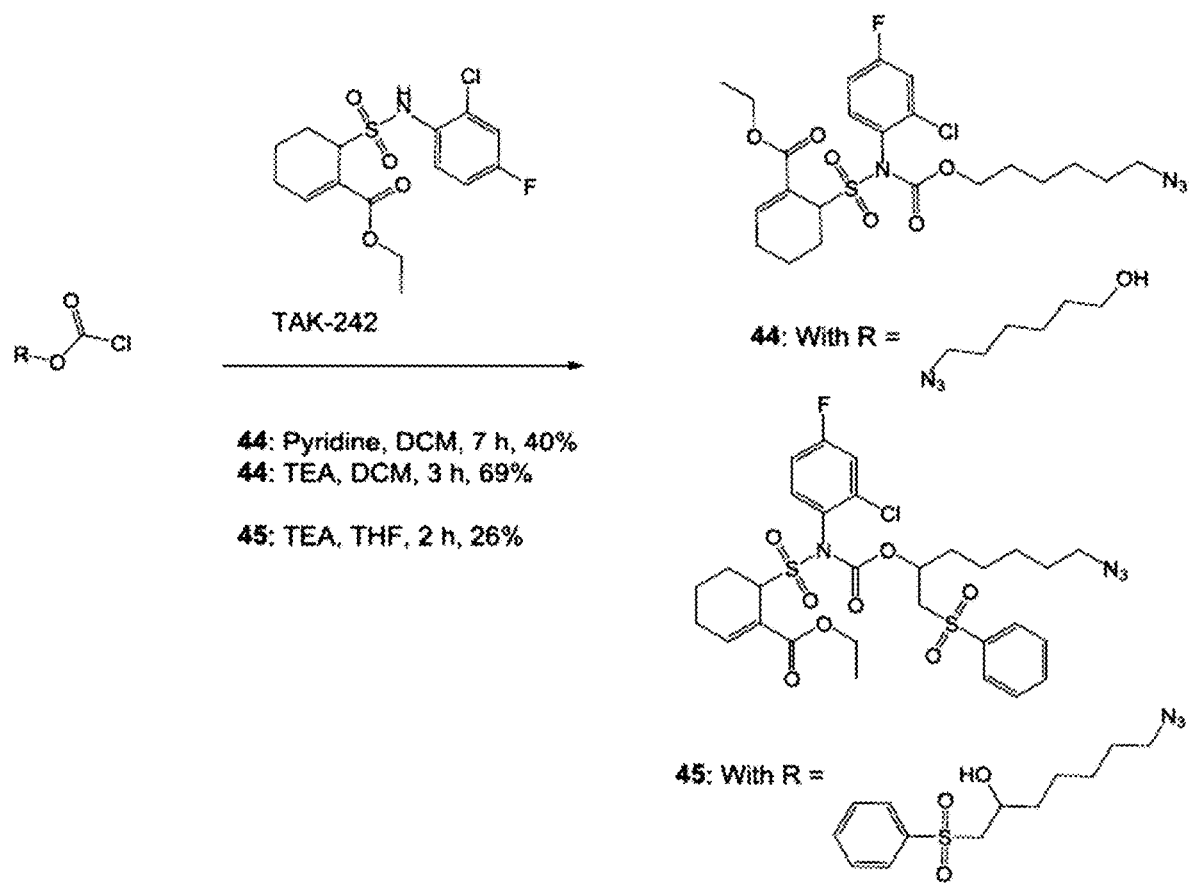
FIG. 2 shows an exemplary synthetic scheme for the synthesis of carbamate compounds 44 and 45 from TAK-242 and chloroformates.

FIG. 2 shows an exemplary synthetic scheme for the synthesis of carbamate compounds 44 and 45 from TAK-242 and chloroformates. To react the linker alcohol (7-azido-1-(phenylsulfonyl)heptan-2-ol) with TAK-242 successfully, a stronger and more hindered base triethylamine was needed, giving compound 45. An improvement in the reaction yield was also recorded when triethylamine was used in the synthesis of carbamate compound 44. The synthesis of the carbamate compound 45 which bears a cleavable group attached to TAK-242 allows use of the drug as a prodrug. The azide functionality on carbamate compound 45 allows the conjugation to islets via click chemistry. FIG. 3 shows an exemplary scheme for the conjugation of modified TAK-242 to islets via a releasable linker.

Figure 4:
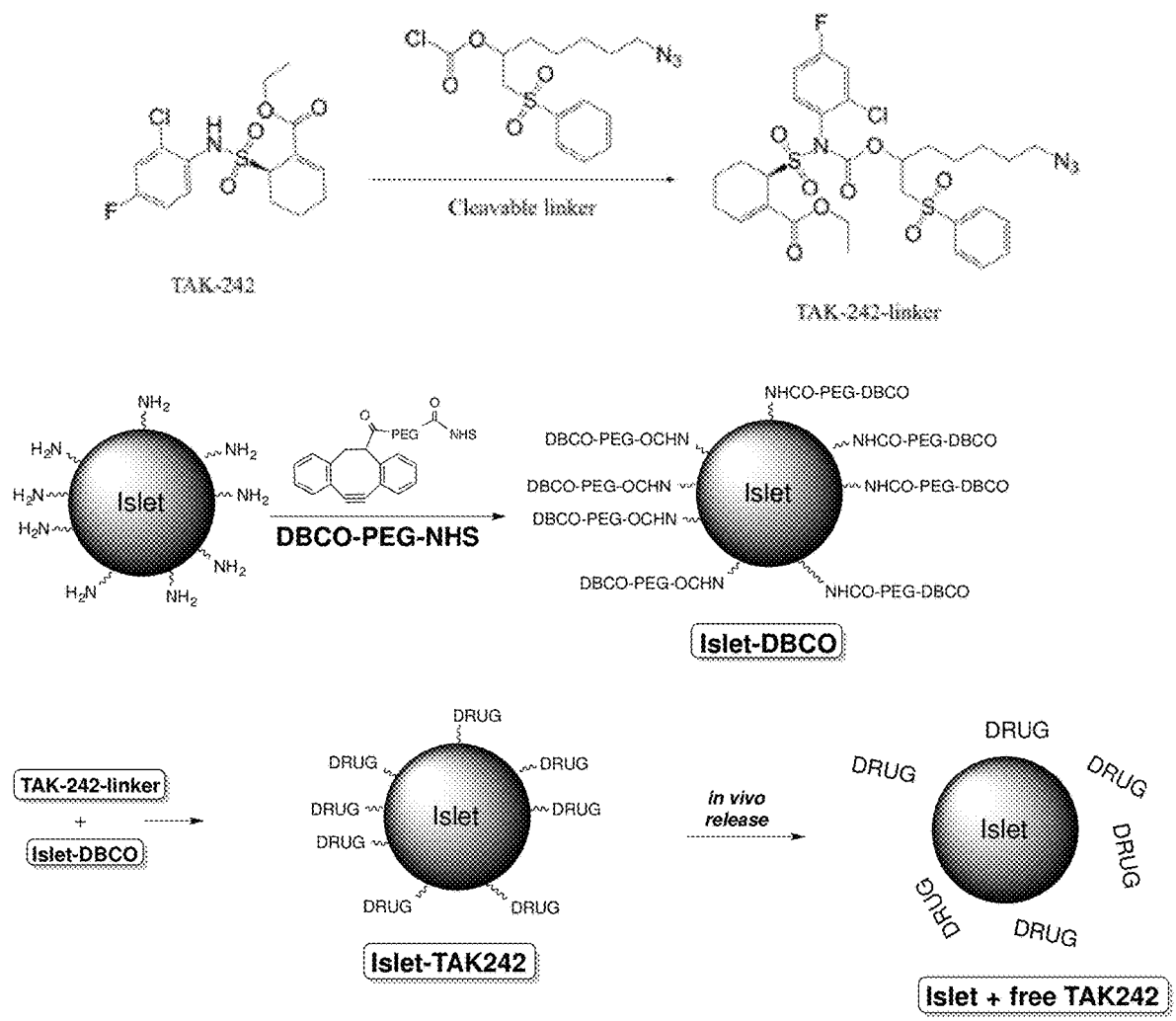
FIG. 4 shows a representative scheme for the modification of dibenzocyclooctyl (DBCO)-modified islets with TAK-242, in accordance with a preferred embodiment of the present methods.

FIG. 4 shows a representative scheme for the modification of dibenzocyclooctyl (DBCO)-modified islets with TAK-242, in accordance with a preferred embodiment of the present methods. DBCO groups are ideal for use in "click" chemistry reactions. DBCO groups react with azide ($N_3$) groups to facilitate connection of the TAK-242 linker compound to the surface of the islet. After transplantation of the surface modified islet, there is in vivo release of the drug TAK-242 from the surface of the islet. This release is "tunable."

In additional embodiments, the linker chemistry could be modified in any suitable ways known to scientists skilled in the field. For example, hydrazine linkers could be used to allow for simple hydrolytic cleavage, or disulfides could be used to allow for the reductive cleavage by endogenous thiols (with the kinetics controlled by adjusting the steric environment of the disulfide). Additionally, enzymatically-cleavable linkers could be used such as esters and peptides. By using a nitro-aryl hypoxia-sensitive linker, drugs could be selectively released based on the oxygen content of the transplant microenvironment.

Additional preferred embodiments include a method for modifying a surface of live tissue intended for transplant with a protective therapeutic agent to produce a modified protected transplant tissue. The method includes obtaining live tissue intended for transplant into a recipient. The live tissue can be any suitable tissue and in preferred embodiments comprises pancreatic islets. A next step includes contacting the surface of the live tissue with a functionalizing compound to create reactive surface moieties on the surface of the live tissue and produce a reactive tissue surface. The functionalizing compound can be any suitable activating or functionalizing compound, including a bi-functional NHS-Alkyne compound or dibenzocyclooctyne-PEG4-N-hydroxysuccinimidyl ester (NHS-PEG4-DBCO). In an additional step the reactive tissue surface is then contacted with a therapeutic-linker compound. The therapeutic-linker compound comprises a therapeutic agent and a releasable linker moiety. Any therapeutic agent can be used, including any suitable anti-inflammatory or immunosuppressive drug, and preferably it can be TAK-242. In preferred embodiments, if the therapeutic agent is TAK-242, then the therapeutic-linker compound can be the TAK-$PhSO_2$-Linker prodrug described herein. Contacting the therapeutic-linker compound with the reactive surface moieties of the reactive tissue surface causes the releasable linker moiety of the therapeutic-linker compound to link the therapeutic-linker compound to the reactive tissue surface and produce modified protected transplant tissue. Once the modified protected transplant tissue is transplanted into a recipient, the releasable linker moiety is cleaved in vivo and the therapeutic agent is locally released.

Example 1

Figure 5:
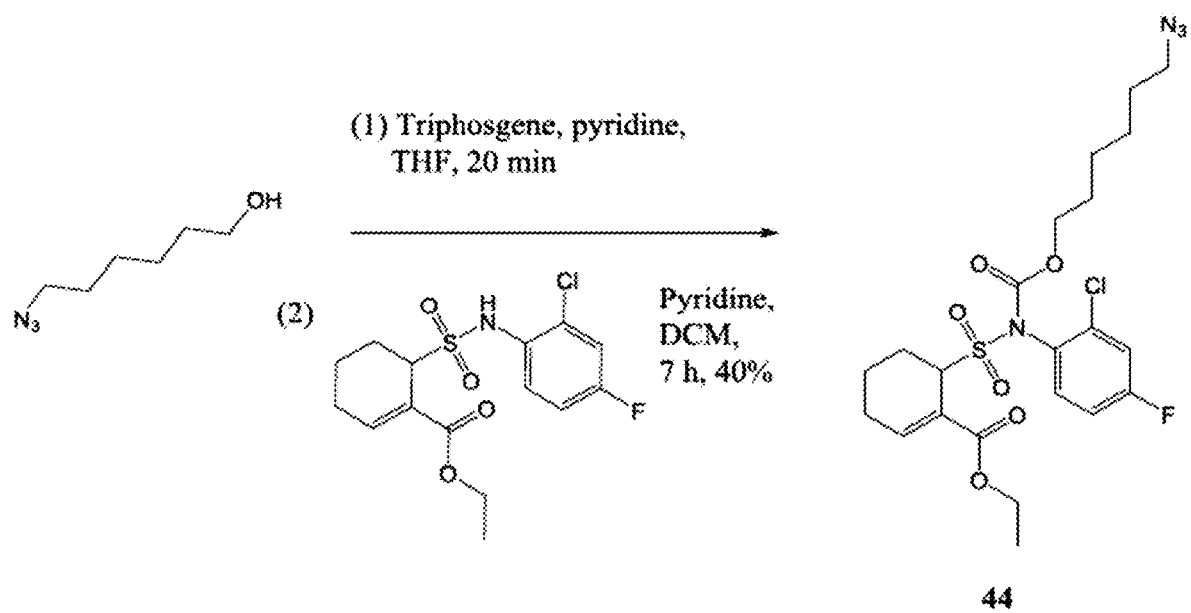
FIG. 5 shows a scheme for the synthesis of compound 44.

Preferred embodiments utilize carbamate compounds 44 and 45 (see FIGS. 2 and 3) in the modification of tissue surfaces with the drug TAK-242. FIG. 5 shows a scheme for the synthesis of compound 44, ethyl 6-(N-(((6-azidohexyl)oxy)carbonyl)-N-(2-chloro-4-fluorophenyl)sulfamoyl) cyclohex-1-ene-1-carboxylate.

Detailed steps in the synthesis were as follows: Pyridine (62 μL, 0.77 mmol) was added dropwise to a stirred solution of 6-azido-1-hexanol (0.056 g, 0.39 mmol) and triphosgene (0.19 g, 0.64 mmol) in 1 ml of anhydrous tetrahydrofuran. The resulting suspension was stirred for 20 minutes and filtered and concentrated to give the crude chloroformate as an oil. To the solution of the crude chloroformate in dichloromethane (3 ml) was added ethyl 6-(N-(2-chloro-4-fluorophenyl)sulfamoyl)cyclohex-1-ene-1-carboxylate (0.128 g, 0.35 mmol) and pyridine (55 μL, 0.68 mmol). The solution was stirred for 7 hours at room temperature and then partitioned between dichloromethane (5 ml) and water (15 ml). The aqueous phase was extracted with dichloromethane (20 ml). The combined organic phases were washed with water (20 ml), dried over magnesium sulfate, concentrated and subjected to by flash chromatography using ethyl acetate/hexanes (20%-25%) to provide 44.

Major isomer (separated peaks): $^1$H NMR (600 MHz, CDCl$_3$) δ 7.38 (1H), 7.23 (1H), 7.19 (1H), 6.96 (1H), 5.41 (1H), 4.32-4.09 (4H), 3.21 (t, J=6.9 Hz, 2H), 2.82 (1H), 2.47 (1H), 2.28 (1H), 2.04 (1H), 1.81-1.73 (2H), 1.62 (2H), 1.53 (2H), 1.31 (7H); $^{13}$C NMR (126 MHz, CDCl$_3$) δ 166.1, 162.3 (d, J=253.1 Hz), 152.1, 148.6, 136.2 (d, J=11.0 Hz), 132.4 (d, J=9.4 Hz), 129.8 (d, J=3.8 Hz), 124.0, 117.5 (d, J=25.8 Hz), 114.7 (d, J=22.3 Hz), 67.7, 61.3, 58.9, 51.2, 28.7, 28.3, 26.1, 25.2, 23.9, 16.8, 14.3.

Minor isomer (separated peaks): $^1$H NMR (600 MHz, CDCl$_3$) δ 7.60 (1H), 7.38 (1H), 7.23 (1H), 7.04 (1H), 5.03 (1H), 4.32-4.08 (4H), 3.21 (t, J=6.9 Hz, 2H), 2.68 (1H), 2.47 (1H), 2.28 (1H), 2.19 (1H), 1.81-1.73 (2H), 1.62 (2H), 1.53 (2H), 1.31 (7H); $^{13}$C NMR (126 MHz, CDCl$_3$) δ 166.0, 162.4 (d, J=253.2 Hz), 152.0, 147.5, 136.3 (d, J=10.9 Hz), 132.1 (d, J=9.6 Hz), 130.5 (d, J=3.9 Hz), 123.8, 117.6 (d, J=25.9 Hz), 114.9 (d, J=22.3 Hz), 67.7, 61.1, 59.5, 51.2, 28.7, 28.2, 26.1, 25.0, 23.7, 16.3, 14.2.

HRMS (+ESI) calcd for $C_{22}H_{28}ClFN_4NaO_6S$ (M+Na$^+$) 553.1294, found 553.1295 (Δ 0.2 ppm).

Figure 6:
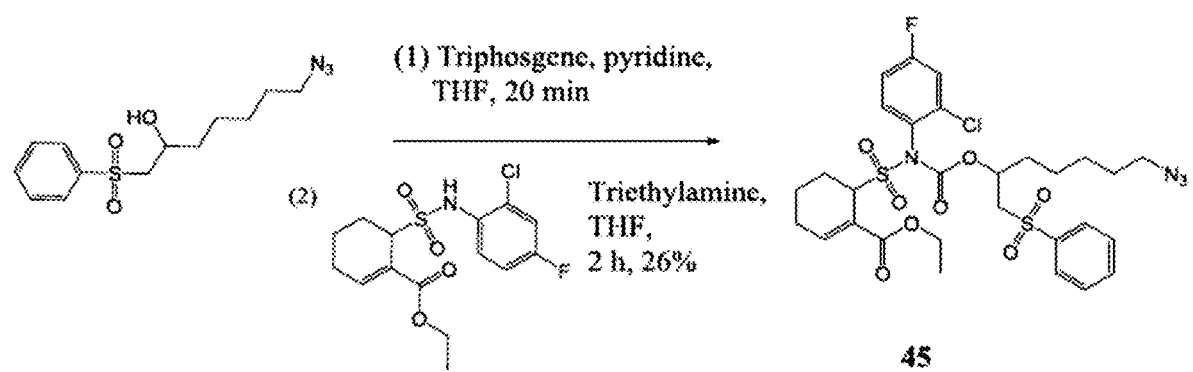
FIG. 6 shows a scheme for the synthesis of compound 45.

FIG. 6 shows a scheme for the synthesis of compound 45, ethyl 6-(N-(((7-azido-1-(phenylsulfonyl)heptan-2-yeoxy)carbonyl)-N-(2-chloro-4-fluorophenyl)sulfamoyl)cyclohex-1-ene-1-carboxylate, also referred to as TAK-PhSO2-Linker prodrug.

Detailed steps in the synthesis were as follows: Pyridine (27.3 μL, 0.34 mmol) was added dropwise to a stirred solution of 7-azido-1-(phenylsulfonyl)heptan-2-ol (45.5 mg, 0.15 mmol) and triphosgene (79 mg, 0.27 mmol) in 2.1 ml of anhydrous tetrahydrofuran. The resulting suspension was stirred for 20 minutes and filtered and concentrated to give the crude chloroformate as an oil. To the solution of the crude chloroformate in tetrahydrofuran (2.5 ml) was added ethyl 6-(N-(2-chloro-4-fluorophenyl)sulfamoyl)cyclohex-1-ene-1-carboxylate (55 mg, 0.15 mmol) and triethylamine (38.4 μL, 0.28 mmol). The solution was stirred for 2 hours at room temperature and diluted with ethyl acetate and washed with 1 M HCl, water, saturated sodium bicarbonate and brine (5 ml each). The organic phase was dried over magnesium sulfate, concentrated and subjected to flash chromatography using ethyl acetate/hexanes (25%-30%) to provide 45.

$^{13}$C NMR (126 MHz, CDCl$_3$) δ 166.3, 166.1, 163.5, 163.5, 161.5, 161.5, 151.4, 151.3, 148.1, 146.8, 139.1, 139.0, 137.0, 136.9, 135.8, 135.7, 134.2, 134.2, 133.8, 133.0, 133.0, 132.2, 132.1, 130.6, 130.6, 129.5, 129.5, 129.5, 129.4, 128.4, 128.3, 127.5, 124.0, 123.6, 118.1, 117.9, 117.6, 117.4, 115.3, 115.1, 114.9, 114.8, 71.8, 71.8, 61.3, 61.2, 59.4, 58.7, 58.6, 58.5, 51.2, 44.6, 33.9, 33.6, 28.6, 26.2, 26.1, 25.2, 24.8, 24.0, 23.9, 23.8, 23.4, 16.8, 16.1, 14.4, 14.3; HRMS (+ESI) calcd for $C_{29}H_{34}ClFN_4NaO_8S_2$ (M+Na$^+$) 707.1383, found 707.1383 (Δ 0.0 ppm).

In examining the proton NMR of compound 44, it appeared that this compound was formed as a mixture of compounds that were structurally similar. A series of characterization experiments were carried out, including COSY (correlation spectroscopy) NMR, carbon-13 NMR, DEPT-135, and multiplicity-edited HSQC to determine the nature of this compound. The results of these experiments were consistent with the existence of two isomers with one being the major and the other being the minor one. The possibility of rotational isomers is depicted in FIG. 7. Compound 45, on the other hand, will exist as diastereomers arising from the two asymmetric centers present in addition to the conformational isomerism.

Figure 8:
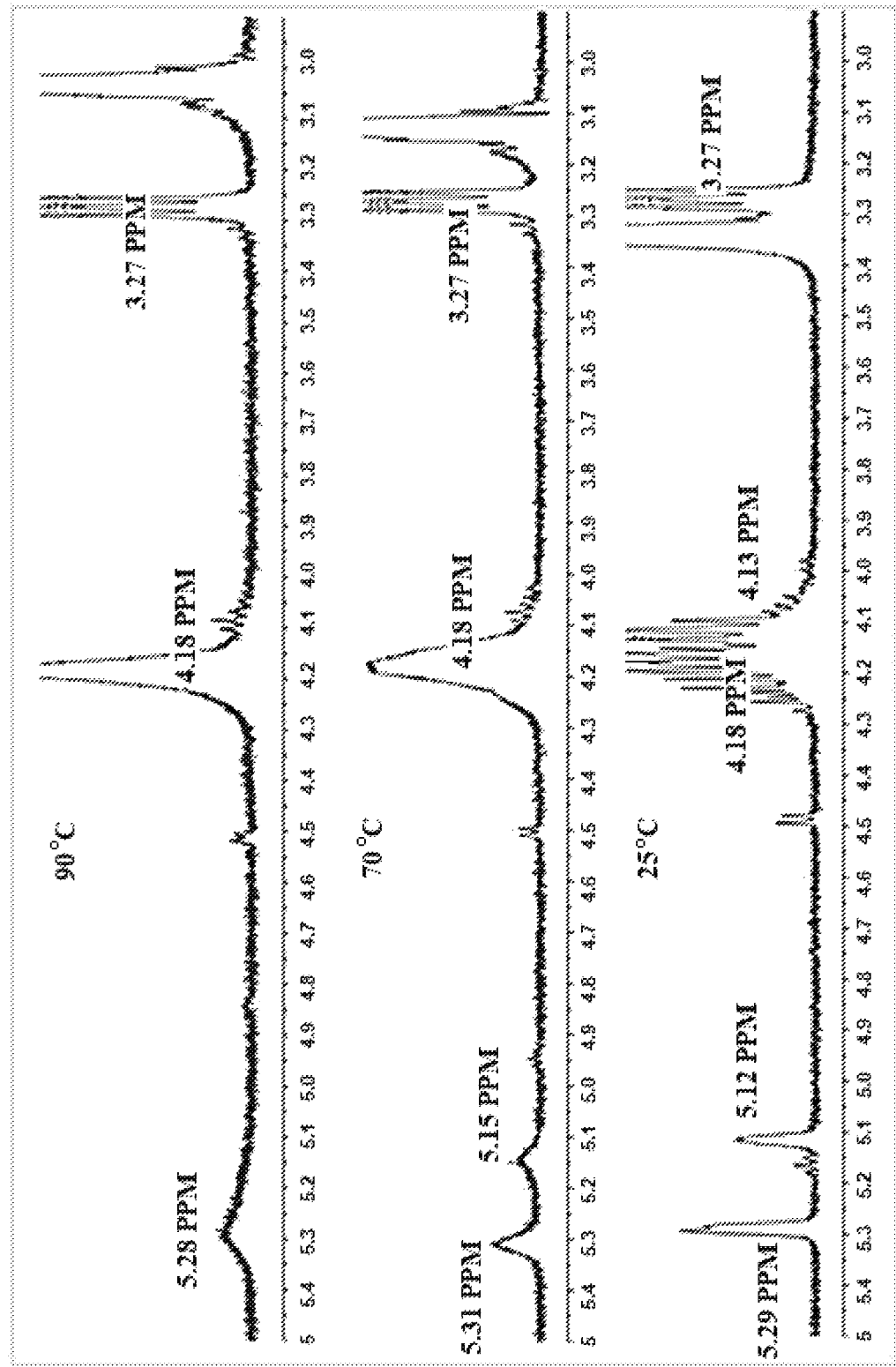
FIG. 8 shows the results of a variable temperature NMR experiment for compound 44.

An experiment was performed to determine if compound 44 was a mixture of rotational isomers, namely, a variable temperature NMR. Proton NMR of 44 was obtained at temperatures 25° C., 35° C., 50° C., 75° C., and 90° C. The tentative assignment for the signal of the proton on the asymmetric carbon was at ~5 ppm. Beginning from 70° C. to 90° C., two separate signals in this region began to coalesce and eventually became one—which was expected as a result of fast rotation and equilibration at higher temperatures. FIG. 8 shows the results of the variable temperature NMR experiment for compound 44 (temperatures: 25° C., 70° C., 90° C., NMR solvent: DMSO-d$_6$).

The observed ratio of the major isomer to the minor isomer of compound 44, according the proton NMR, was 1: ~0.37 in CDCl$_3$ and 1:0.65 in DMSO-d6. The proton NMR assignments were determined using $^1$H NMR, COSY, $^{13}$C NMR, and edited HSQC ($^1$H—$^{13}$C) spectra.

Figure 9:
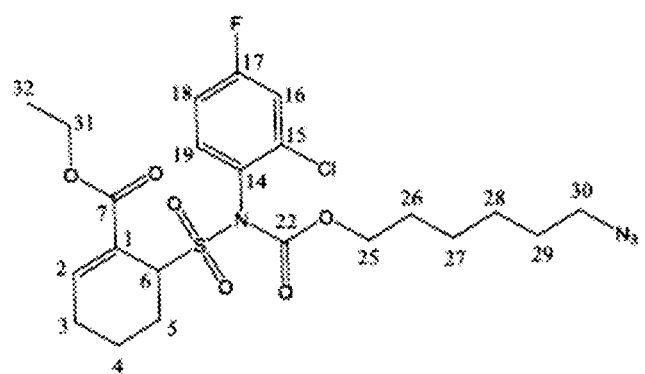
FIG. 9 shows the general numbering of the protons and carbons of compound 44 for spectral assignment purposes.

FIG. 9 shows the general numbering of the protons and carbons of compound 44 for spectral assignment purposes. The assignment of peaks in the aromatic region of the proton NMR spectrum of 44 is presented in Table 1 below. This assignment was carried out according to measurements of coupling constants. The coupling constant values are consistent with standard values for H—H and H—F couplings.

TABLE 1

| Proton index number | Type of Coupling | J value (Hz) |
| --- | --- | --- |
| 19 | HC—C(H)—CF | 5.5 |
|  | HC—CH | 8.8 |
| 16 | HC—CF | 8.0 |
|  | HC—C(F)—CH | 2.8 |
| 18 | HC—CH | 8.6 |
|  | HC—C(F)—CH | 2.7 |
|  | HC—CF | Not observed |

The assignment of carbon-13 NMR peaks for compound 44, determined using $^1$H NMR, $^{13}$C NMR, and edited HSQC ($^1$H—$^{13}$C) spectra, is shown in Table 2 below. Additionally, Table 3 below shows the assignment of peaks in the aromatic region of the carbon NMR spectrum according to measurements of coupling constants. The coupling constant values were consistent with standard values for C—F couplings.

TABLE 2

| Carbon index number | δ (ppm) | Line(s) for major isomer (ppm) | Line(s) for minor isomer (ppm) |
| --- | --- | --- | --- |
| 32 | 14.18, 14.30 | 14.30 | 14.18 |
| 4 | 16.28, 16.80 | 16.80 | 16.28 |
| 5 | 23.70, 23.87 | 23.87 | 23.70 |
| 3 | 25.03-25.23 | 25.20 | 25.03 |
| 27, 28 | 26.13 |  |  |
| 26 | 28.22, 28.29 | 28.29 | 28.22 |
| 29 | 28.68 |  |  |
| 30 | 51.24 |  |  |
| 6 | 58.92, 59.49 | 58.92 | 59.49 |
| 31 | 61.10, 61.29 | 61.29 | 61.10 |
| 25 | 67.67, 67.73 | 67.73 | 67.67 |
| 18 | 114.64-114.96 | 114.64, 114.82 | 114.78, 114.96 |
| 16 | 117.35-117.74 | 117.35, 117.56 | 117.53, 117.74 |
| 1 | 123.77, 123.97 | 123.97 | 123.77 |
| 14 | 129.75-130.49 | 129.75, 129.78 | 130.46, 130.49 |
| 19 | 132.04-132.45 | 132.38, 132.45 | 132.04, 132.12 |
| 15 | 136.14-136.35 | 136.14, 136.23 | 136.27, 136.35 |
| 2 | 147.49, 148.61 | 148.61 | 147.49 |
| 22 | 152.00, 152.11 | 152.11 | 152.00 |
| 17 | 161.28-163.38 | 161.28, 163.29 | 161.37, 163.38 |
| 7 | 166.02, 166.08 | 166.08 | 166.02 |

TABLE 3

| Carbon index number | Type of Coupling | J value (Hz) |
|---|---|---|
| 17 | 1-bond coupling | 253 |
| 14 | 4-bond coupling | 3.8 |
| 15 | 3-bond coupling | 11 |
| 19 | 3-bond coupling | 9.4 |
| 18 | 2-bond coupling | 22.3 |
| 16 | 2-bond coupling | 25.8 |

For compound 45, while the ratio of isomers present, according to proton NMR, is approximately 1:1 in DMSO-d6, this ratio is close to 1:0.7 in CDCl$_3$.

Example 2

Preferred embodiments of the present methods have been tested in conjunction with pancreatic islets, small clusters containing an average of about 1000 cells that contain several cell types (including the beta cells responsible for insulin production and regulation). Pancreatic islet cell transplantation is used to restore glycemic control in patients with type 1 diabetes. This procedure requires islets from the pancreas of a deceased organ donor to be purified and processed before transplantation into the liver of a patient via the portal vein. If successful, transplantation of pancreatic islets help type 1 diabetes patients achieve glucose regulation and insulin independence. Long-term benefits of improved glucose control include prevention of known complications of diabetes including heart disease, kidney disease and microvascular damage. While islet transplantation can successfully restore glycemic control to patients with type 1 diabetes (or who have undergone a pancreatectomy), the survival of transplanted islets, and therefore the clinical success of this procedure, is often threated by the immediate blood-mediated inflammatory responses (IB-MIR) 1-2 days immediately post-transplant.

Pancreatic islet cell transplantation is currently considered experimental due to considerable side effects and risk of complications. Transplanted islets are at risk due to inflammatory responses and hypoxia in the microenvironment that threaten survival. In addition to these assaults on the transplanted cells, patients are susceptible to bleeding, blood clots and long term side effects from immunosuppressive drugs that are necessary due to the allogenic nature of the transplant. Immunosuppressive drugs are typically administered systemically in bolus and are non-selective in action, often resulting in damage to tissues throughout the body.

This method protects pancreatic islet cells for transplantation, leading to a reasonable expectation that the method may be used generally for organ transplant and/or to protect implanted biomaterials. This method has potential to increase islet engraftment by 25-100%, which may effectively promote insulin independence as well as eliminate the need for multiple islet transfusions for type 1 diabetes patients.

Preliminary experiments on bovine pericardium using densitometry suggest that densities on the order of at least nmol/mm$^2$ are achievable in the attachment of compounds to tissue surfaces. This indicates that therapeutically relevant localized drug concentrations are readily accessible. The release of the drug at the tissue surface also greatly enhances the local concentration.

Figure 10:
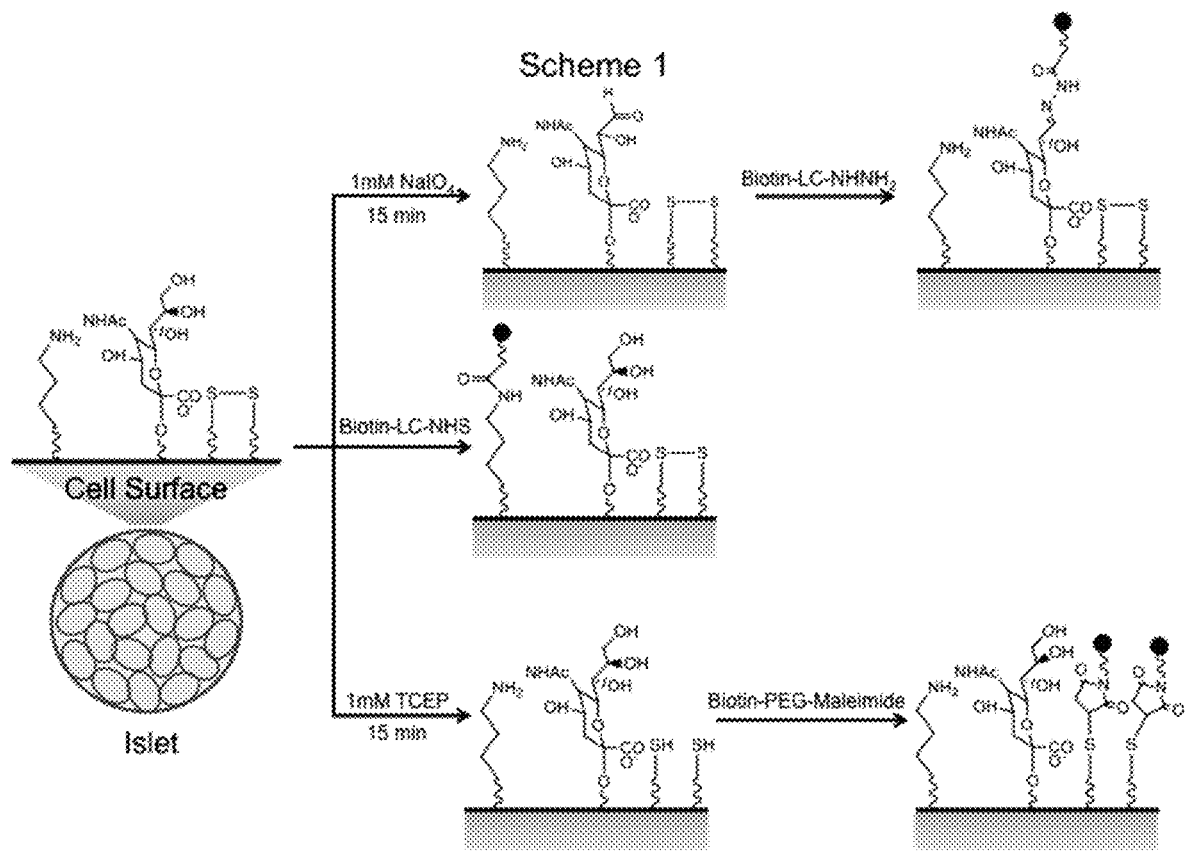
FIG. 10 shows representative schemes for these kinds of islet surface modifications, using biotin as a marker.
Figure 11:
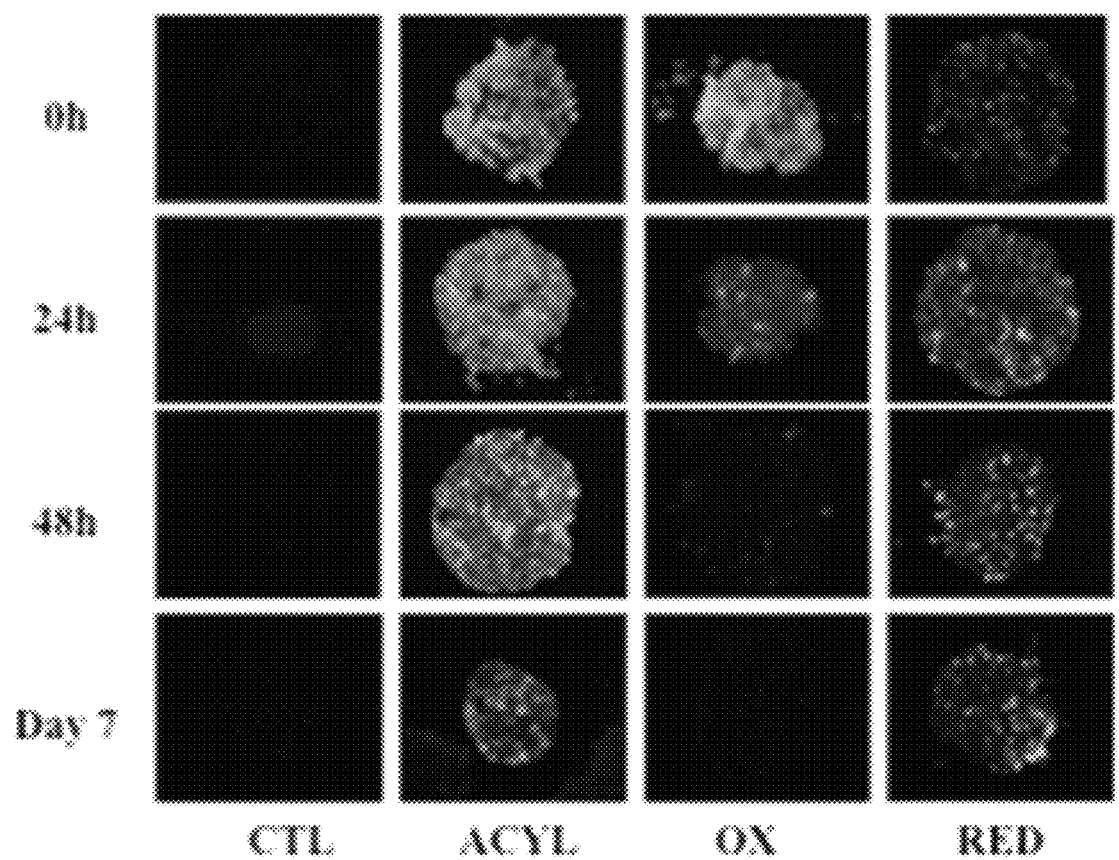
FIG. 11 shows fluorescence images of murine islets 0-7 days after surface modification using NHS esters (ACYL), periodate oxidation/hydrazide condensation (OX) and TCEP reduction/maleimide (RED), with a control (CTL).
Figure 12A:
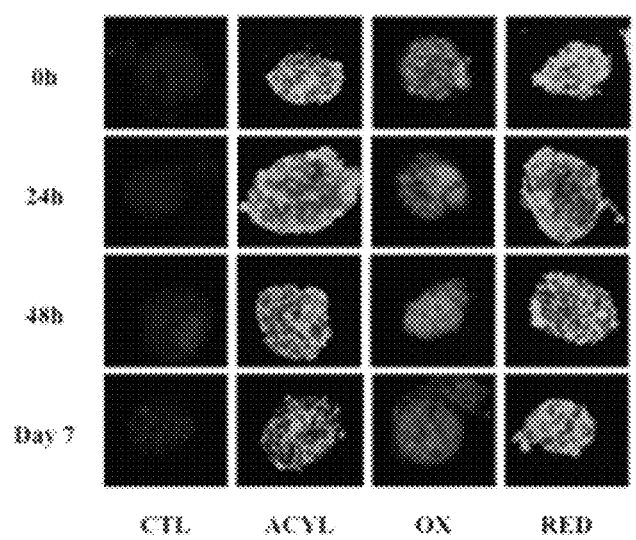
FIG. 12A shows fluorescence images of human islets 0-7 days after surface modification using NHS esters (ACYL), periodate oxidation/hydrazide condensation (OX) and TCEP reduction/maleimide (RED), with a control (CTL).
Figure 12B:
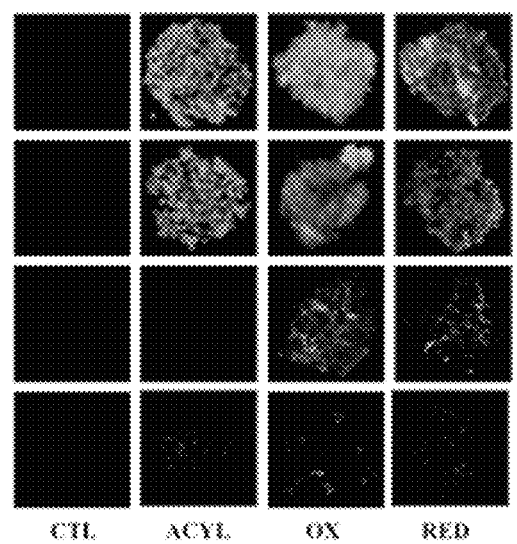
FIG. 12B shows fluorescence images of porcine islets 0-7 days after surface modification using NHS esters (ACYL), periodate oxidation/hydrazide condensation (OX) and TCEP reduction/maleimide (RED), with a control (CTL).

The durable and biocompatible covalent modification of murine, porcine, and human islets using active esters, maleimides (after treatment with the reducing agent TCEP), and hydrazides (after mild periodic acid oxidation) has been accomplished. FIG. 10 shows representative schemes for these kinds of islet surface modifications, using biotin as a marker. FIG. 11 shows fluorescence images of murine islets 0-7 days after surface modification using NHS esters (ACYL), periodate oxidation/hydrazide condensation (OX) and TCEP reduction/maleimide (RED), with a control (CTL). FIG. 12A shows fluorescence images of human islets 0-7 days after surface modification using NHS esters (ACYL), periodate oxidation/hydrazide condensation (OX) and TCEP reduction/maleimide (RED), with a control (CTL). FIG. 12B shows fluorescence images of porcine islets 0-7 days after surface modification using NHS esters (ACYL), periodate oxidation/hydrazide condensation (OX) and TCEP reduction/maleimide (RED), with a control (CTL).

Figure 13:
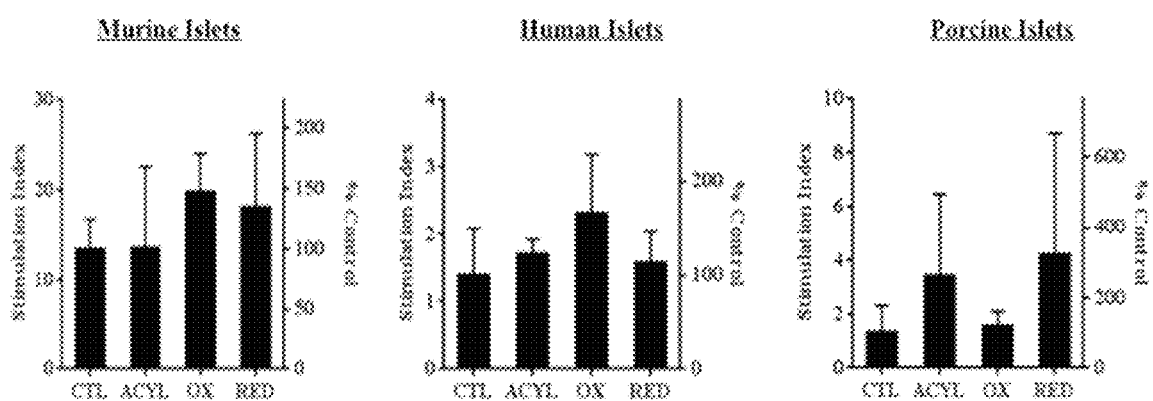
FIG. 13 shows the retained function (release of insulin upon glucose stimulation) of murine islets, human islets, and porcine islets modified using NHS esters (ACYL), periodate oxidation/hydrazide condensation (OX) and TCEP reduction/maleimide (RED), with a control (CTL) lacking the modification.

Surface modified islets were also demonstrated to be viable and to function. FIG. 13 shows viability of murine islets, human islets, and porcine islets modified using the same modifications, namely NHS esters (ACYL), periodate oxidation/hydrazide condensation (OX) and TCEP reduction/maleimide (RED), with a control (CTL) lacking the modification, and Hoechst 33342 and propidium iodide stains. Fluorescence images of the islets confirmed attachment of the stains.

Figure 14:
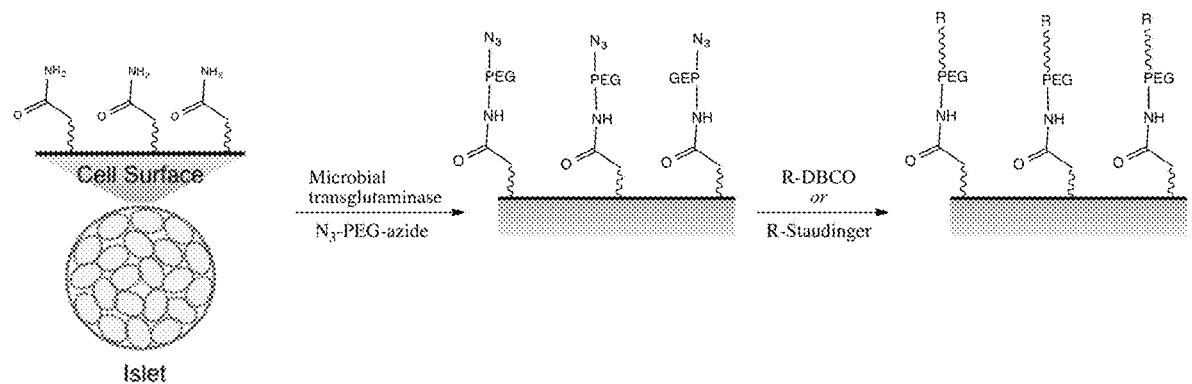
FIG. 14 shows a representative scheme for this enzymatic modification of islets.

Additional non-toxic modification techniques have been demonstrated, including the enzymatic transamination of surface glutamine residues using a transglutaminase. FIG. 14 shows a representative scheme for this enzymatic modification of islets.

Figure 15:
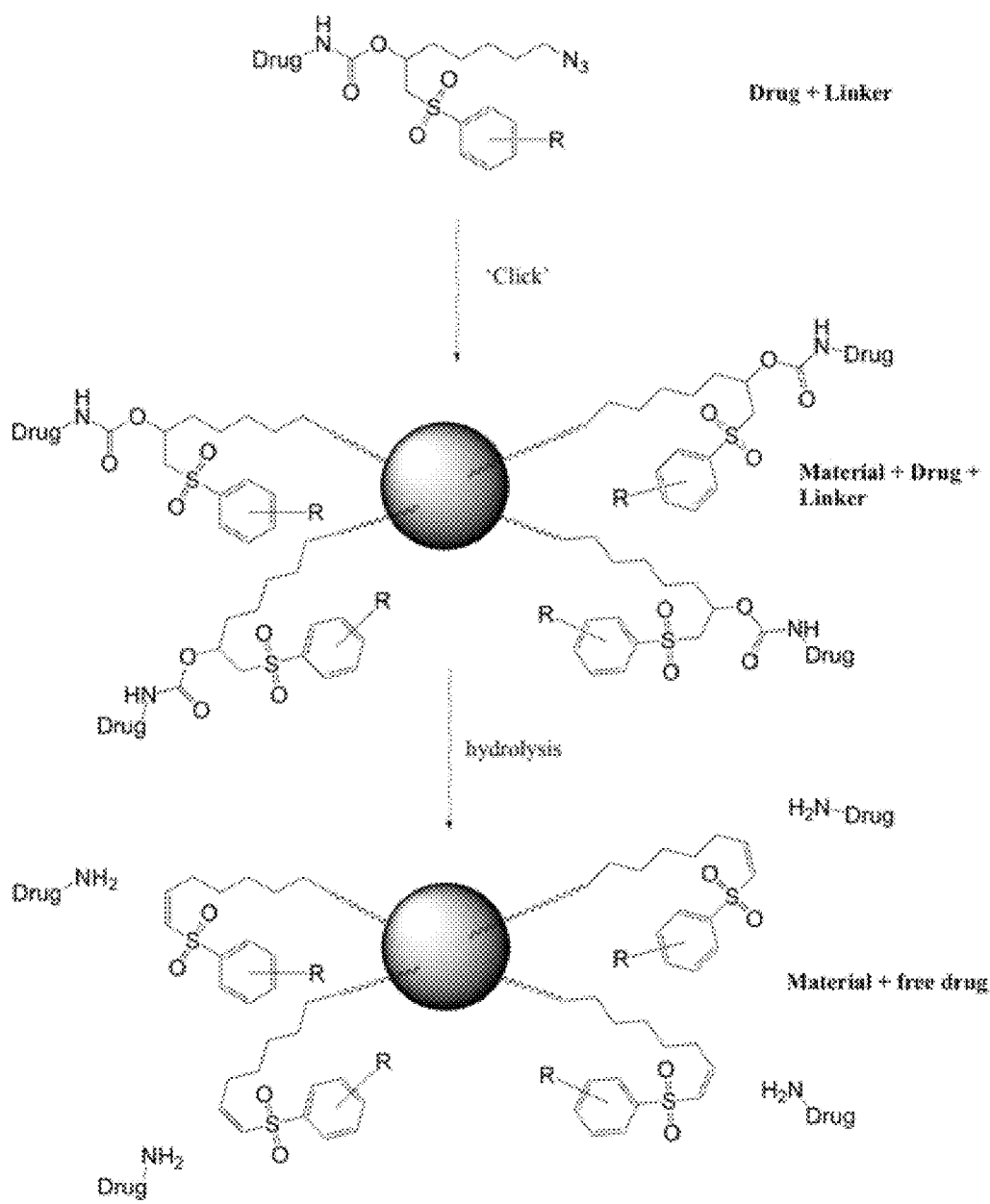
FIG. 15 shows a representative scheme for attachment and subsequent release of a drug, such as TAK-242, modified with the releasable linker used in compound 45, to surfaces of a material using simple "click" chemistry.
Figure 16:
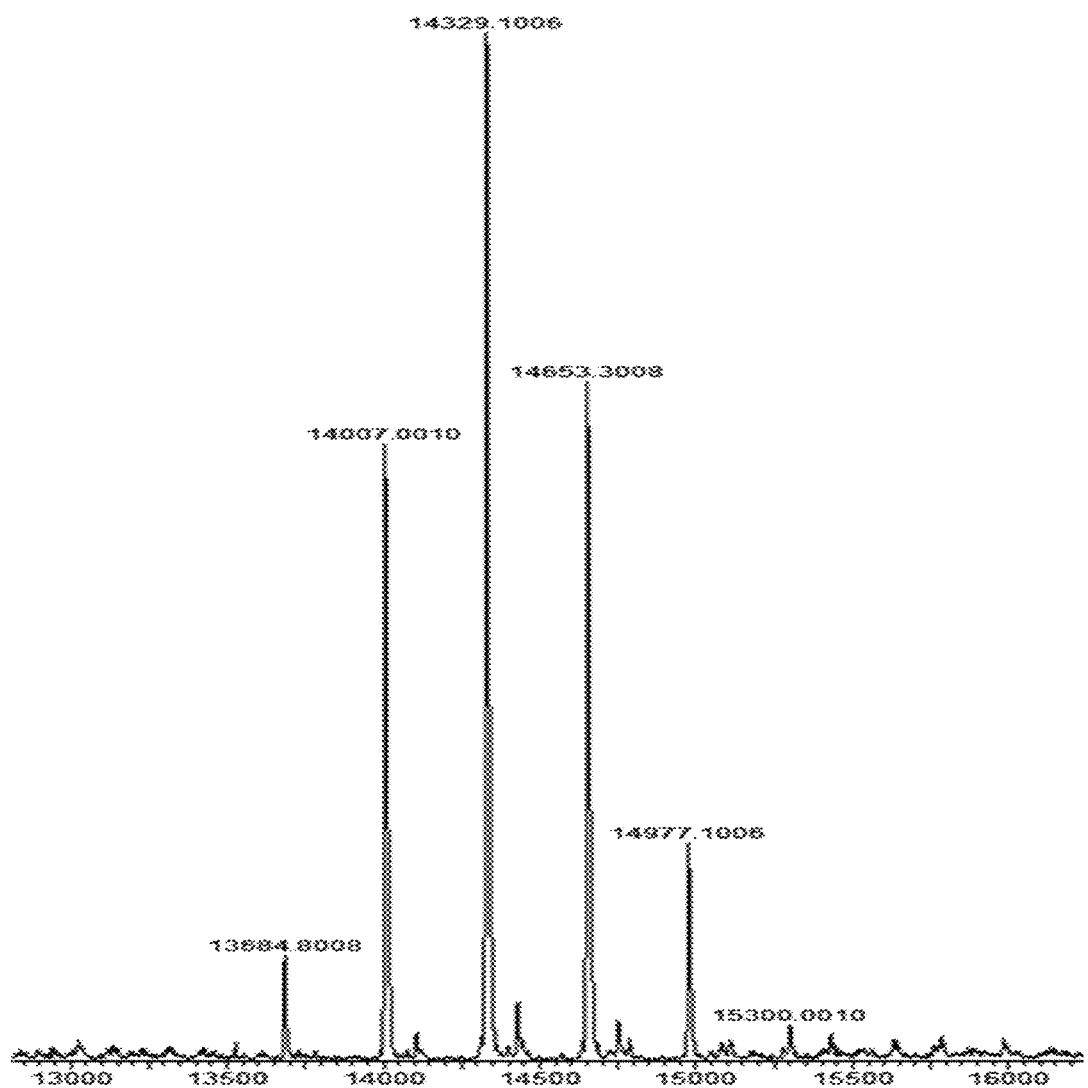
FIG. 16 shows a protein (RNAse A) modified with zero to four linkers after one hour.
Figure 17:
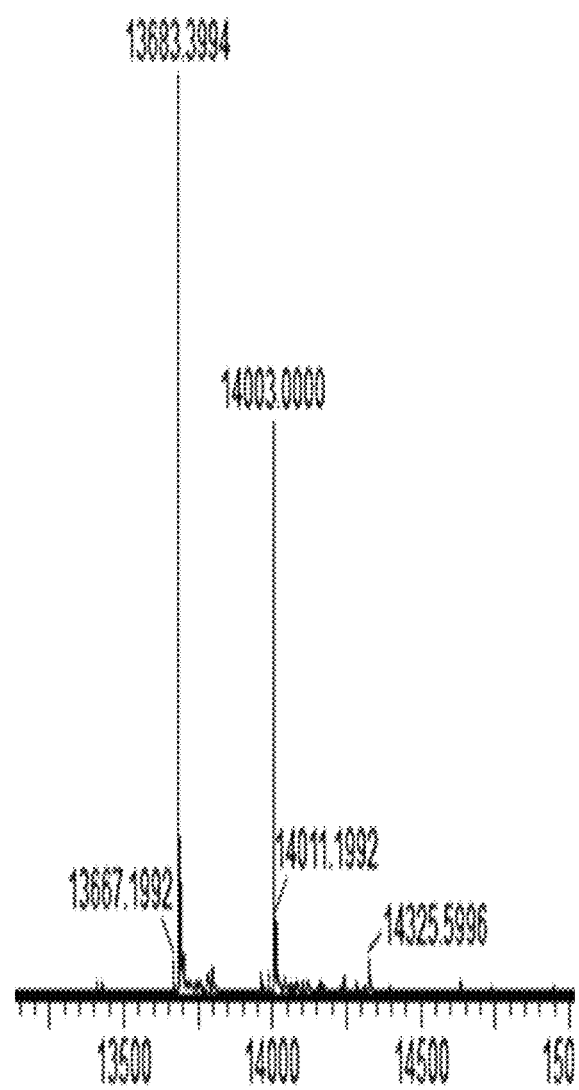
FIG. 17 shows the same protein sample as FIG. 16 showing the hydrolytic release of 2 modifications after one week in solution.

The small-molecule drug TAK-242 is considered an appropriate immunosuppressive drug for use in surface modification of tissue for transplant, particularly pancreatic islets. TAK-242 is an anti-inflammatory drug and a TLR4 agonist. The structure of TAK-242 is shown in FIG. 2, along with a scheme for producing compound 45, which includes the drug TAK-242 attached to a linker. FIG. 15 shows a representative scheme for attachment of a drug, such as TAK-242, modified with the linker used in compound 45, to surfaces of a material using simple "click" chemistry. As shown in FIG. 15, hydrolysis releases the drug from the linker. FIG. 16 shows the hydrolytic release of four linkers after one hour, and FIG. 17 shows the hydrolytic release of 2 linkers after one week. As shown in FIG. 15, hydrolysis releases the drug from the linker. FIG. 16 shows the hydrolytic release linker molecules from the protein RNAse A. At one hour the mass spectrum of modified RNAse shows that four linker molecules are attached. FIG. 17 shows that only 2 linkers remain attached to the RNAse A after one week.

Example 3

Mouse islets can be quickly and efficiently labelled with a fluorophore using NHS-based "click" chemistry. The islet surface is first activated using a bi-functional NHS-Alkyne compound having the structure shown below.

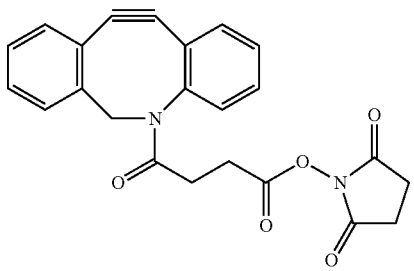 [SMILES: O=C(CCC(=O)N1Cc2ccccc2C#Cc2ccccc21)ON1C(=O)CCC1=O]

Figure 18:
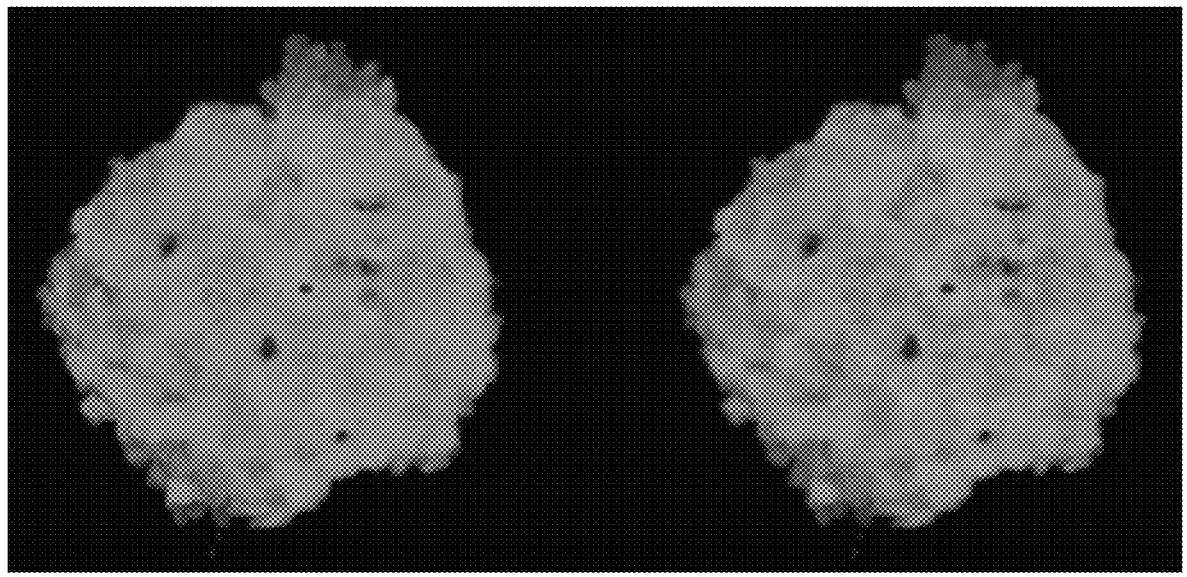
FIG. 18 shows images of, on the left, an islet labelled with a 488 nm fluorophore and on the right, a labelled islet overlaid with nuclear DAPI stain.

NHS reacts with the islet surface while the alkyne moiety remains freely exposed on the surface. Then, a 488 nm fluorophore with a terminal $N_3$ is added to the islets which readily reacts with the alkyne moiety, undergoing a spontaneous Huisgen-cycloaddition reaction. Rinsed islets are then plated on a microscope slide with nuclear DAPI stain and imaged. FIG. 18 shows images of, on the left, an islet labeled with a 488 nm fluorophore and on the right, a labeled islet overlaid with nuclear DAPI stain. The results in FIG. 18 show that in just a short time, islets can be efficiently labeled using this NHS-based "click" chemistry.

Example 4

Figure 19:
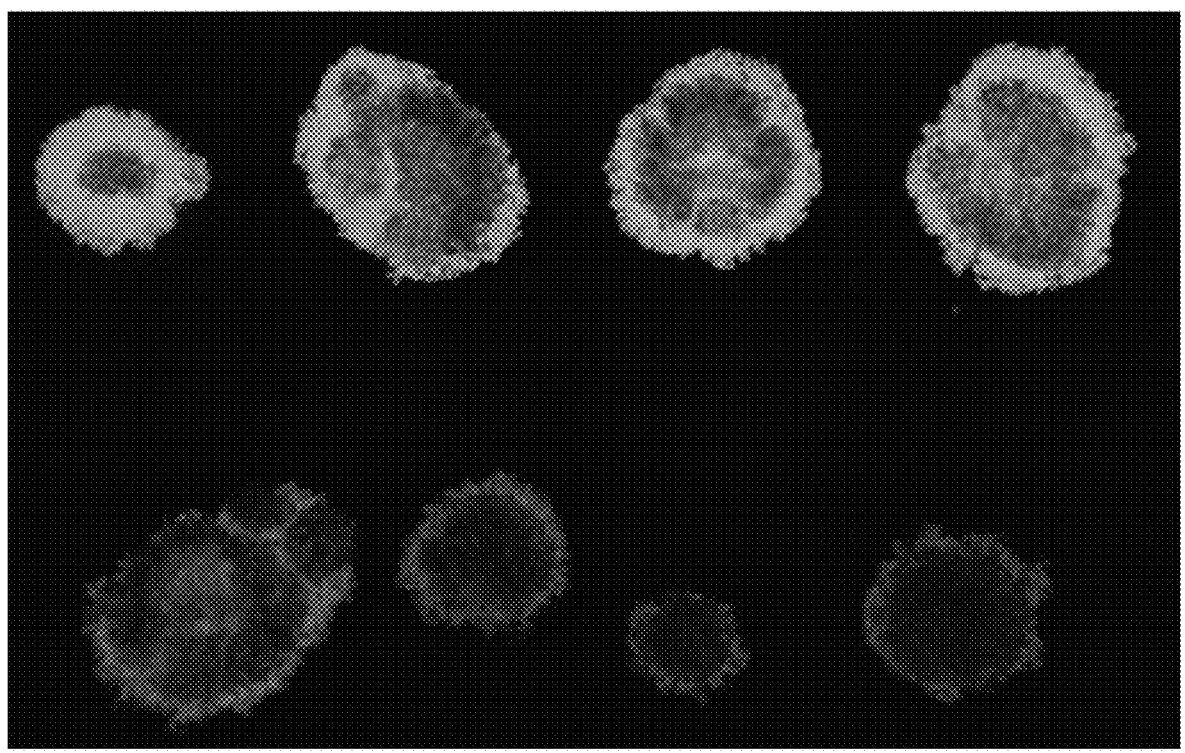
FIG. 19 shows, on the top, islets labelled with a 488 nm fluorophore and, on the bottom, islets reacted with the TLR4-antagonist TAK-242 compound followed by a 488 nm fluorophore.

The modified TAK-242 compound (compound 45) binds to the islets in the same fashion as outlined in Example 3. One group of murine islets were modified first with the NHS-Alkyne and then the 488 nm fluorophore. A second group were first modified with the NHS-Alkyne, then with the TAK-242 compound, and then with the 488 nm fluorophore. FIG. 19 shows, on the top, alkyne-modified islets labeled with a 488 nm fluorophore and, on the bottom, alkyne-modified islets reacted with the TLR4-antagonist TAK-242-linker compound followed by a 488 nm fluorophore. The "hollow" appearance of labeling in the center of the islets is due to contact with the microscope slide coverslip and the 3-dimensional size of the islets. As the images in FIG. 19 show, the fluorophore labeling of islets first reacted with the NHS-alkyne (bottom row) is significantly reduced when compared to islets modified directly with the fluorophore (top). The results show that efficient modification of islets can be accomplished with the TAK-242 compound via NHS-based "click" chemistry.

Example 5

This example demonstrates the extended protection of modified islets in vitro. Compared to free TAK-242 pretreatment, the TAK-Linker compound covalently attached to the islet surface provides extended protection. In this experiment, the protected status of murine islets was compared 24 hrs after treatment with free TAK-242 (TAK LPS), the releasable conjugated TAK-242 (TAK-Linker LPS), or the more stable hexanol-conjugated TAK-242 (TAK-HexOH LPS).

First, islets were modified with either TAK-Linker or TAK-HexOH (1 hr NHS-DBCO followed by 1 hr TAK compounds), or treated with free TAK-242 (3 uM, 30 min @37° C.). All islets were rinsed with culture media (RPMI 1640, 10% FBS) prior to culturing. After overnight culture, the treated groups were challenged with LPS (2 ug/mL, 4 hrs @ 37° C.), a TLR4-specific agonist, and compared to unprotected islets (LPS) and unprotected/untreated control islets.

Figure 20:
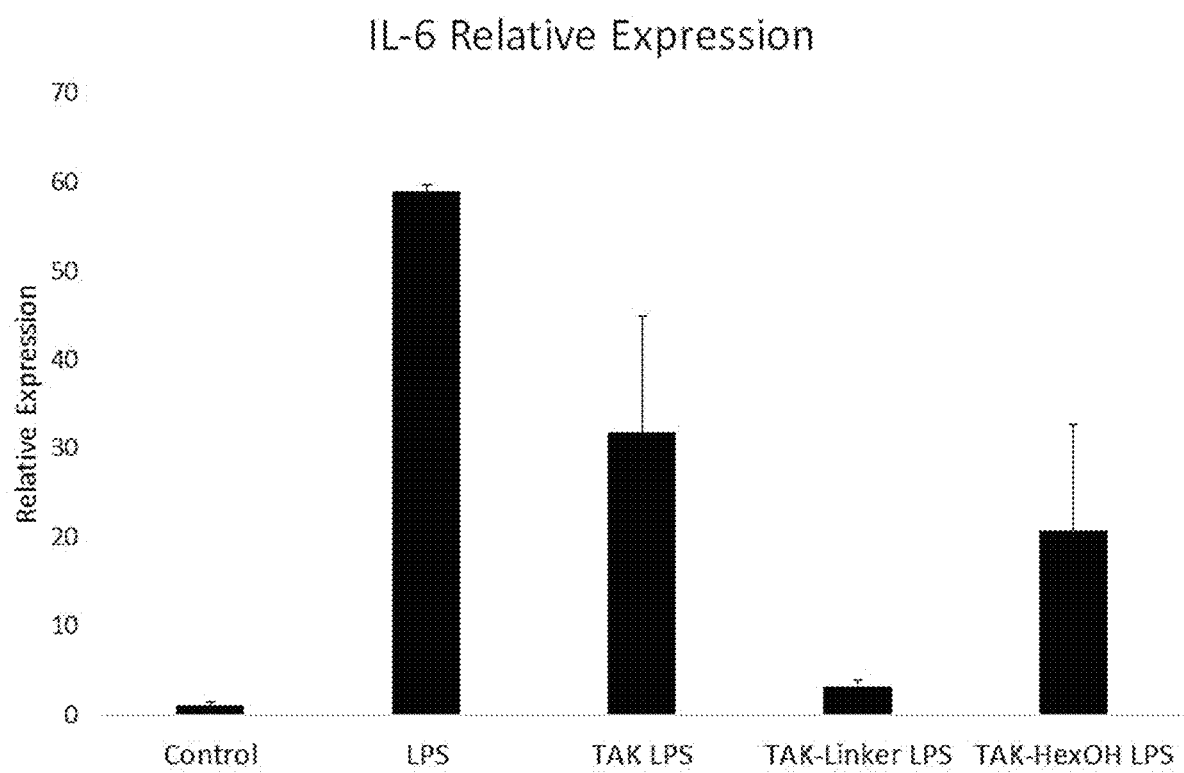
FIG. 20 shows the relative expression of IL-6 for islets modified with either TAK-Linker or TAK-HexOH or treated with free TAK-242, compared to unprotected islets (LPS) and unprotected/untreated control islets.

Total RNA was isolated from the islets for mRNA analysis. The gene expression of cytokine IL-6 was used for evaluation due to its key role in acute inflammation. FIG. 20 shows the relative expression of IL-6 for each group. Islets modified with the TAK-Linker had only a ~3-fold increase in IL-6 expression compared to the unprotected islets which had a ~59-fold increase. Additionally, the TAK-linker provided significantly more protection than islets treated with free TAK-242 (~32-fold increase). The TAK-HexOH provided similar protection to free TAK-242. The results here show that the releasable compound provides significant extended protection to islets.

Example 6

Figure 21:
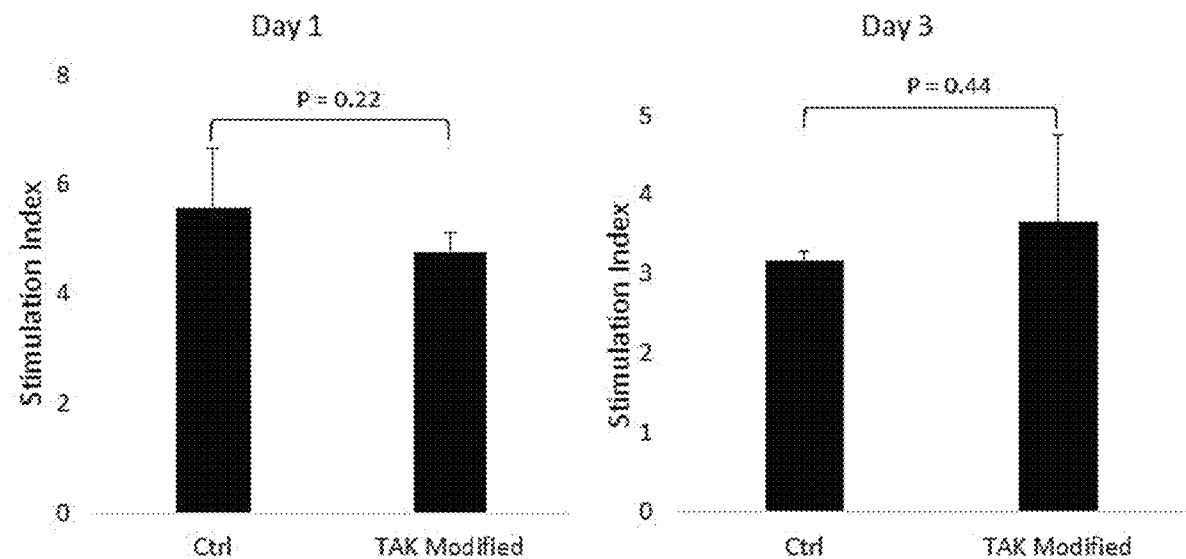
FIG. 21 shows the stimulation index for nmodified (Ctrl) or modified (TAK Modified) islets subjected to low-glucose and subsequent high-glucose solution at day 1 and day 3.

This example shows retention of endocrine function of modified islets. To examine whether the modification of islets affects their viability and function, a glucose-stimulated insulin-secretion (GSIS) assay was performed. Unmodified (Ctrl) or modified (TAK Modified) murine islets were subjected to low-glucose and subsequent high-glucose solutions. Insulin secreted by islets was measured in the glucose solutions by ELISA. The stimulation index was calculated as the average ratio of insulin secreted in the high glucose solution over insulin secreted in low glucose. This GSIS assay was performed 24 hrs and 72 hrs after modification. FIG. 21 shows the stimulation index results. The results show that the modified islets retain similar endocrine function to normal control islets.

Example 7

Figure 22:
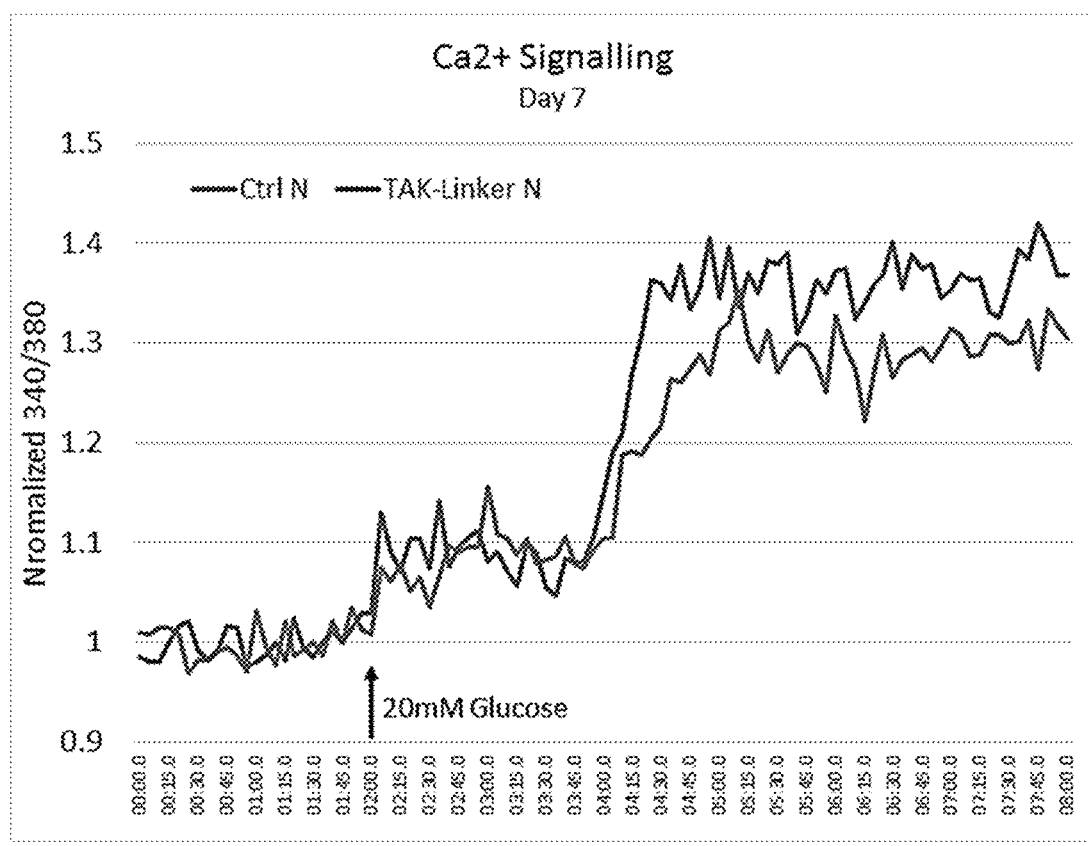
FIG. 22 shows intracellular Ca2+ signaling for control and modified islets.

This example demonstrates the function of modified islets. In addition to GSIS in the previous example, islet function was also assayed using Fura-2 to quantify intracellular Ca2+ signaling in response to glucose challenge. Control and modified murine islets were both dissociated and cultured overnight in a 96-well plate. The next day, they were pre-incubated with Fura-2 AM in low glucose (2 mM) buffer for 1 hour to load the islets with Fura-2 and to equilibrate them to the lower glucose level. The islets were then rinsed with low glucose buffer (without Fura-2 AM) and loaded into the fluorescent plate reader. The wells were read every 5 seconds for 2 minutes to form the baseline before high glucose buffer (20 mM final) was injected into the wells and monitored for another 6 minutes. Data was recorded as the ratio of the 340 nm/380 nm excitation, 508 nm emission ratio. Results for intracellular Ca2+ signaling for control and modified islets are shown in FIG. 22. The results indicate that even 7 days after modification, the modified islets display similar, if not superior intracellular Ca2+ signaling in response to glucose challenge.

Example 8

This example shows in vivo transplant of syngeneic modified islets. To assess the function and viability of the modified islets in an animal model, 200 modified or unmodified islets from C57B1/6 mice were transplanted into the kidney sub-capsular space of diabetic C57B1/6 mice. The number of islets (200) represents a "marginal" dose of islets that typically provide sub-optimal glucose control.

Figure 23A:
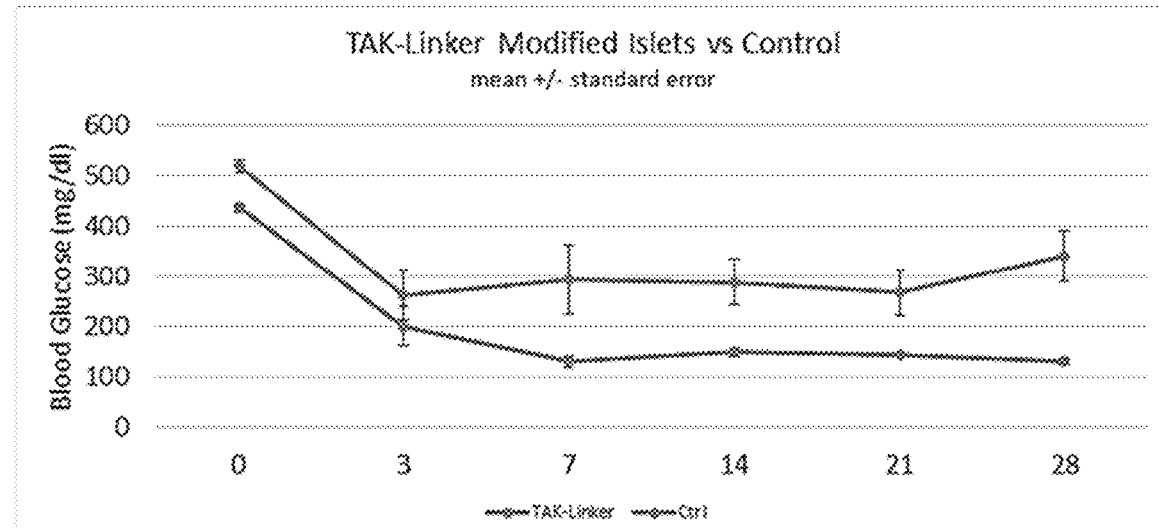
FIG. 23A shows blood glucose as monitored by tail-vein prick of diabetic mice transplanted with modified TAK-Linker islets and unmodified control islets over the course of a month, as the average of all samples.
Figure 23B:
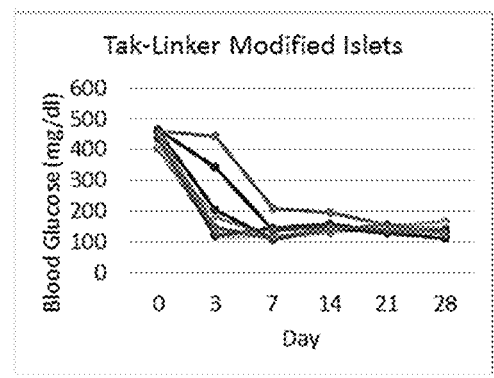
FIG. 23B shows blood glucose of individual mice transplanted with modified TAK-Linker islets.
Figure 23C:
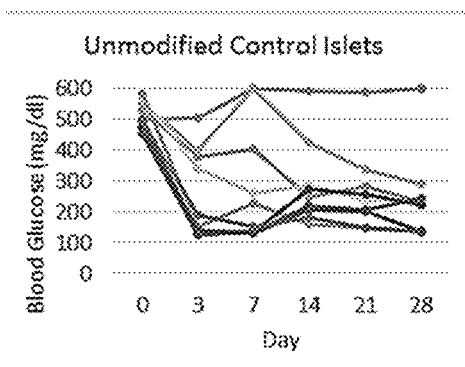
FIG. 23C shows blood glucose of individual mice transplanted with unmodified control islets.
Figure 23D:
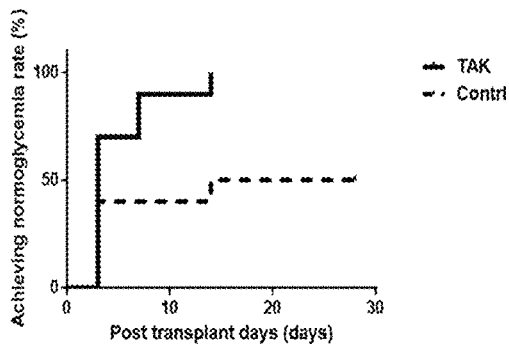
FIG. 23D shows the rate of achieving normalglycemia, defined as two consecutive blood glucose reading of <200 mg/dL, for mice receiving modified TAK-Linker islets and unmodified control islets.

Blood glucose was monitored by tail-vein prick approximately once a week for a month. The results are shown as the average of all samples (FIG. 23A), individual samples (FIG. 23B, FIG. 23C), and the rate of achieving normalglycemia (FIG. 23D), defined as two consecutive blood glucose reading of <200 mg/dL.

Figure 23E:
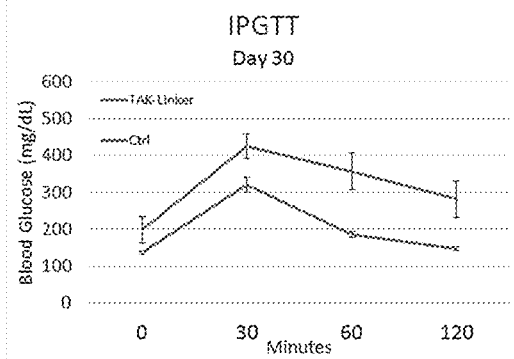
FIG. 23E shows results of an intra-peritoneal glucose tolerance test (IPGTT) performed to assess the insulin response to glucose administered directly to fasting mice receiving modified TAK-Linker islets and unmodified control islets.

On day 30, an intra-peritoneal glucose tolerance test (IPGTT) was performed to assess the insulin response to glucose administered directly to fasting mice (FIG. 23E).

The results from this experiment demonstrate that the modified islets have superior function and viability after transplant compared to the unmodified control islets.

Example 9—General Materials and Methods

In Examples 10-16 below, reagents used for synthesis were purchased from Acros Organics (Pittsburgh, Pa., USA), Alfa Aesar (Haverhill, Mass., USA), Sigma-Aldrich (St. Louis, Mo., USA), VWR (Radnor, Pa., USA), and Pierce (Waltham, Mass., USA). Solvents were obtained from the Baylor Sciences Building stockroom and distilled before use. Liquid chromatography-mass spectrometry (LC-MS)—grade methanol from Fisher Scientific (Hampton, N.H., USA) was used for running MS experiments. Reactions were monitored by thin-layer chromatography (TLC) using silica XG TLC plates with UV254 from Sorbent Technologies (Norcross, Ga., USA), and the final products were purified by flash chromatography using silica gel 60 (230-400 mesh) purchased from Alfa Aesar. A Varian 500 MHz nuclear magnetic resonance (NMR) spectrometer (Varian Medical Systems, Palo Alto, Calif., USA) running VNMRJ 2.2C and an AVANCE III HD Bruker 600 MHz NMR spectrometer (Bruker, Billerica, Mass., USA) were used to obtain 1H and 13C NMR data. Chemical shifts were reported in ppm (δ), and coupling constants (J) were expressed in Hz. General high-resolution mass spectra (HRMS) were obtained using the electrospray ionization (ESI) technique on an LTQ Orbitrap Discovery mass spectrometer (Thermo Scientific, Waltham, Mass., USA) in the Baylor University Mass Spectrometry Core Facility.

Mouse islet isolation. Islets were isolated from 7- to 8-week-old male C57BL/6 mice (Envigo) by common-bile duct cannulation, using a 27G needle, and pancreatic perfusion with Collagenase Type V (1 mg/mL; Sigma-Aldrich, St. Louis, Mo., USA) in Hank's balanced salt solution (HBSS; Mediatech) followed by pancreatectomy and digestion in a water bath at 37° C. for 20 min with periodic agitation by hand. Digested pancreatic tissue was washed twice with HBSS supplemented with 5 mM glucose, 20 mM HEPES, 0.5% bovine serum albumin, and 1% penicillin/streptomycin (Sigma-Aldrich) and filtered through a 600-micron mesh strainer. Islets were purified using a discontinuous Biocoll Separating Solution gradient (1.077 and 1.100 g/mL; Biochrom GmbH). Islets were hand-picked to >95% purity before culturing in Roswell Park Memorial Institute medium (RPMI) 1640 supplemented with 10% fetal bovine serum plus 1% penicillin/streptomycin solution (Sigma-Aldrich) at 37° C. and 5% CO2. Islets were cultured overnight (12-18 h) prior to use in experiments.

Intraperitoneal glucose tolerance test. IPGTT was conducted on day 30 post—islet transplant to assess graft function. Mice were placed in fresh cages with access to water ad libitum but no food and fasted for 6 h. Then, 2 g/kg of glucose in a 20% solution was administered to the mice intraperitoneally, mimicking a postprandial glucose bolus. Blood glucose was checked prior to glucose administration at time 0 and then at 30, 60, 90, 120, and 150 min following administration. AUC response in blood glucose was then calculated between each group.

TAK-242 inhibition of inflammation in an ischemia-reperfusion model. In the ischemia/reperfusion injury model, pancreases were perfused with collagenase alone (1 mg/kg) or with TAK-242 (3 μM), resected, and preserved on ice for an additional 30 min before isolating islets cultured as described above. After 4 h of culture, gene expression was analyzed as described above.

Viability immunofluorescence staining. For viability assays, islets were stained with 1 μg/mL Hoechst 33342 and 1 μg/mL propidium iodide (Sigma-Aldrich) in DPBS for 30 min at 37° C. Islets were washed twice with DPBS for 5 min before mounting on slides. Images were acquired with a fluorescent microscope (FSX100, Olympus, Tokyo, Japan) with exposure set to auto. ImageJ software was used to count stained cells. Viability was calculated as the percentage of propidium iodide—positive cells out of total Hoechst 33342-positive cells per image.

Modified islet function assays. Glucose-stimulated insulin secretion was assessed on days 1 and 2 postmodification. TAK-PhSO$_2$-Linker modified and unmodified control islets (n=10 per sample) were placed in a 8 μm cell strainer and then incubated with low glucose (1.67 mM) for 1 h to equilibrate the islets, low glucose again for 1 h, and then high (16.7 mM) glucose solution in Krebs-Ringer bicarbonate HEPES buffer (KRBH)+0.2% bovine serum albumin at 37° C. Media samples were collected immediately after islet incubation and frozen at −30° C. until analysis. Insulin content was measured with a mouse insulin enzyme-linked immunosorbent assay kit (ALPCO Diagnostics, Salem, N.H., USA) in duplicate. The stimulation index was calculated as the concentration of insulin in high-glucose solution divided by the insulin concentration in low glucose solution after equilibration.

To measure intracellular Ca2+ signaling, TAK-PhSO$_2$-Linker modified and control islets were dissociated with Accutase (Innovative Cell Technologies, San Diego, Calif.) 6 days postmodification and seeded on a 96-well plate. After overnight culture, islet cells were incubated with fura-2AM (Thermo Fisher, Waltham, Mass., USA) in low glucose (2 mM) KRBH for 1 h at 37° C. After fura-2AM incubation, well contents were dumped out and fresh low glucose KRBH was added to the cells. A basal 340 nm/380-508 nm excitation-emission ratio was measured in the cells for 2 min every 5 sec with a Cytation 5 (Biotek, Winooski, Vt., USA). At 2 min, a high-glucose (40 mM) solution was injected into the wells to bring the final glucose concentration to 20 mM. The 340 nm/380-508 nm excitation-emission ratio was continuously monitored for another 6 min. The 340/380 emission ratio was normalized to the basal mean.

Statistical analysis. All data are presented as the mean±standard error of the mean (SEM). Single pairwise comparisons were performed using the two-tailed Student's t test in Microsoft Office Excel 2016. One-way analysis of variance with Tukey's test or Newman-Keuls test was performed for multiple comparisons, and Kaplan-Meier survival function curves were compared using the Mantel-Cox log rank method with GraphPad Prism 7.0 for Windows. Statistical significance was defined as P<0.05.

Example 10—TAK-242 AS TLR4 Antagonist

Figure 24A:
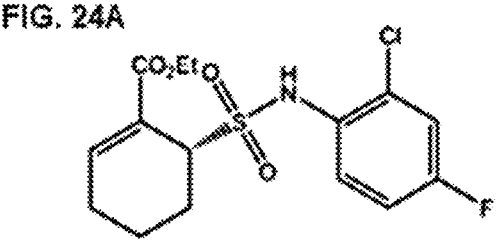
FIG. 24A shows a chemical structure of TAK-242.

To initially investigate whether free TAK-242 can protect islets from TLR4-mediated inflammation, inflammatory responses in islets from C57BL/6 mice challenged with the canonical TLR4 ligand lipopolysaccharide (LPS) were examined. As discussed in detail below, islets were treated with TAK-242 (3 μM for 30 min) before a 24-h challenge with a high dose of LPS (2 μg/mL). After 24 h, culture media was analyzed by multiplex assay, and mRNA was isolated from islet cells for analysis by real-time polymerase chain reaction (RT-PCR). FIG. 24A shows the chemical structure of TAK-242.

Figure 25:
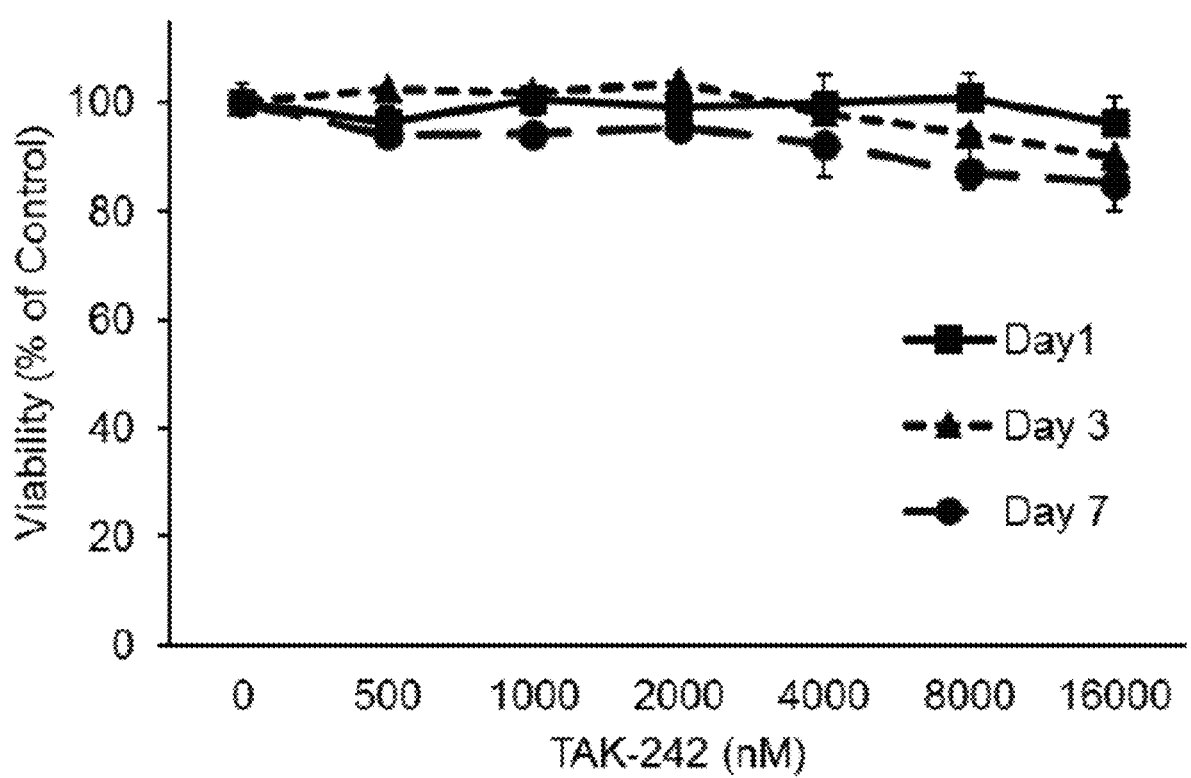
FIG. 25 shows toxicity of TAK-242 to beta cells at 1, 3, and 7 days.

In preliminary testing, TAK-242 showed negligible toxicity to the beta cells at effective concentrations. FIG. 25 shows an assessment of the toxicity of TAK-242 to beta cells. TAK-2 showed negligible toxicity to the beta cells at effective concentrations. MIN6 cells were seeded in a 96-well plate at 15,000 cells per well in RPMI. After overnight culture, culture media was replaced with media containing the indicated TAK-242 concentrations. The control (0 nM TAK-242) contained 0.1% DMSO. Media was changed on day 3. On days 1, 3, and 7, an MTT viability assay was performed. Data are represented as means±SEM. P>0.05 for all samples (one-way ANOVA with Tukey's multiple-comparisons test).

Materials and Methods. After overnight culture, islets were washed in Dulbecco's PBS (Caisson Labs, Smithfield, Utah, USA) before treatment with TAK-242 (3 μM, 30 min; MedchemExpress) and 2 μg/mL LPS-EB (Ultrapure from Escherichia coli O111:B4; Invivogen) for 24 h at 37° C. and 5% CO2. Islets were washed once with cold Dulbecco's PBS immediately after treatment, and total RNA was isolated from samples using TRIzol (Invivogen) and converted to cDNA using a high capacity cDNA reverse transcription kit (Applied Biosystems) following manufacturer protocols. Quantitative expression of genes of interest was determined using RT2 SYBR Green qPCR master mix (Qiagen) on a Bio-Rad CFX Connect (Bio-Rad) with the following program: 95° C., 10 min and 40 cycles of 95° C., 15 sec, 60° C., 1 min. Primers for quantitative real-time PCR analysis were purchased from commercially available stock from Integrated DNA Technologies (Coralville). Relative gene expression was calculated using the 2-ΔΔCT method normalized to 18S mRNA. Cytokines from assay culture media were analyzed using Milliplex MCYTOMAG-70K Assay (EMD Millipore). Samples were prepared following manufacturer guidelines. Analysis was performed after overnight incubation at 4° C. on a Luminex 200 (Luminex). Samples were assayed in triplicate and analyzed in triplicate for cDNA or in duplicate for multiplex assay.

Figure 24B:
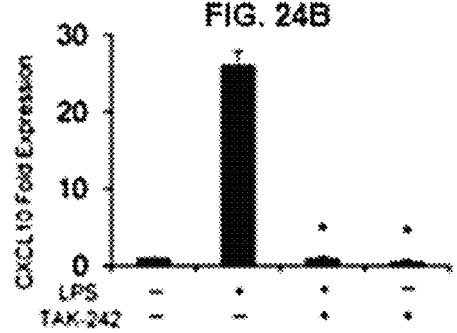
FIG. 24B shows mRNA analysis of proinflammatory cytokines CXCL10 in mouse islets with or without 3 μM TAK-242.
Figure 24C:
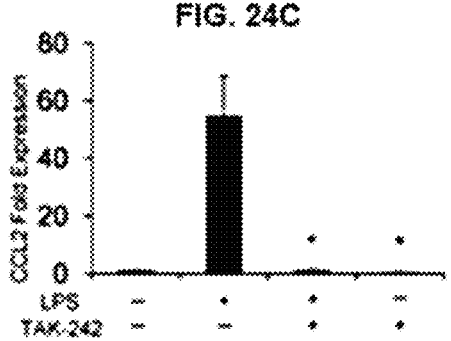
FIG. 24C shows mRNA analysis of proinflammatory cytokines CCL2 in mouse islets with or without 3 μM TAK-242.
Figure 24D:
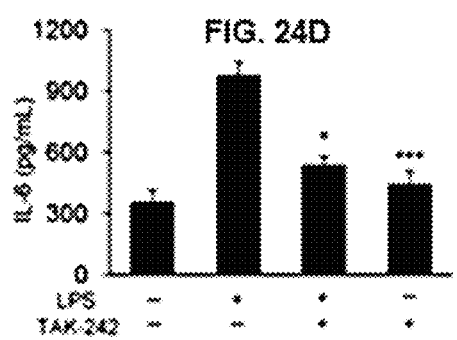
FIG. 24D shows supernatant analysis of proinflammatory cytokine IL-6 after LPS challenge in mouse islets with or without TAK-242.
Figure 24E:
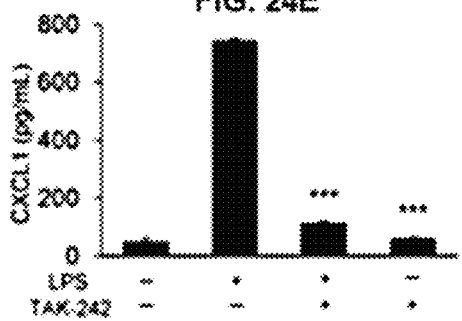
FIG. 24E shows supernatant analysis of proinflammatory cytokine CXCL1 after LPS challenge in mouse islets with or without TAK-242.
Figure 24F:
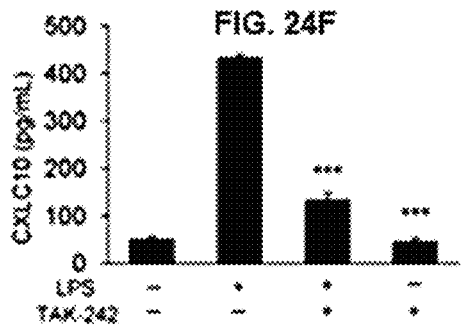
FIG. 24F shows supernatant analysis of proinflammatory cytokine CXCL10 after LPS challenge in mouse islets with or without TAK-242.
Figure 24G:
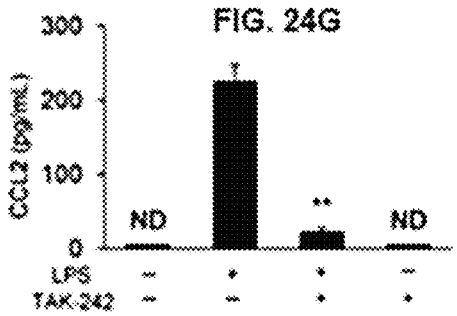
FIG. 24G shows supernatant analysis of proinflammatory cytokine CCL2 after LPS challenge in mouse islets with or without TAK-242.
Figure 24H:
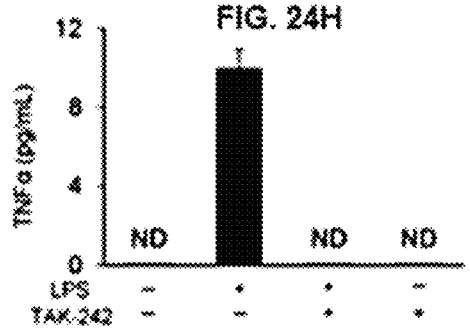
FIG. 24H shows supernatant analysis of proinflammatory cytokine TNF-α after LPS challenge in mouse islets with or without TAK-242.

Gene expression analysis showed LPS-treated islets had significantly increased expression of both CXCL10 and CCL2 (26- and 55-fold, respectively), which was completely blocked by the TAK-242 pretreatment (0.91- and 1.01-fold, respectively; P<0.05) (FIG. 24B-24C). FIGS. 24B and 24C show the mRNA analysis of proinflammatory cytokines CXCL10 and CCL2 in mouse islets 24 h after 2 μg/mL LPS challenge with or without 3 μM TAK-242. FIG. 24D-24H show supernatant analysis of proinflammatory cytokines IL-6, CXCL1, CXCL10, CCL2, and TNF-α 24 h after LPS challenge with or without TAK-242. n=3 per condition. Graphs represent means±SD (*P<0.05, P<0.01, *P<0.001, two-tailed unpaired t test). ND means not detected.

Figure 26A:
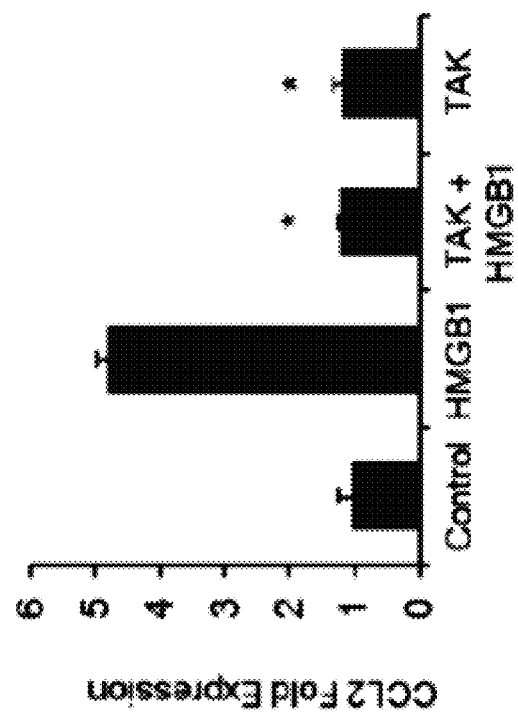
FIG. 26A shows gene expression analysis for proinflammatory gene CXCL10 in mouse islets after challenge with or without TAK-242.
Figure 26B:
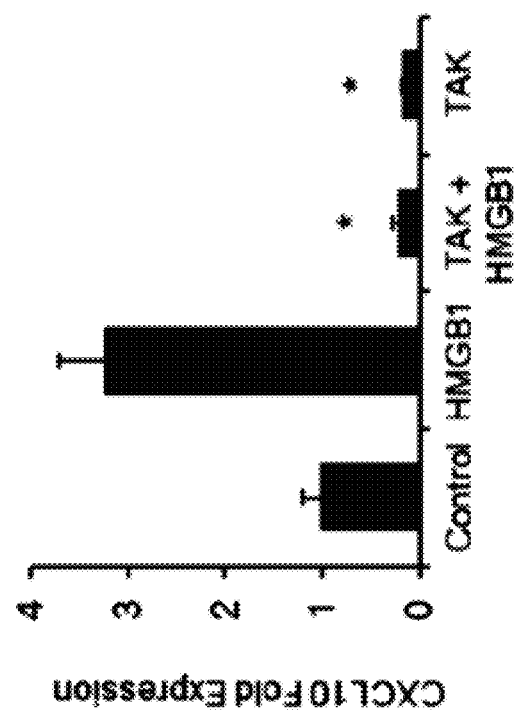
FIG. 26B shows gene expression analysis for proinflammatory gene CCL2 in mouse islets after challenge with or without TAK-242.

Similar results were observed when islets were challenged with high-mobility group box 1 (HMGB1; FIG. 26), an endogenous damage-associated molecular pattern (DAMP) known to elicit acute inflammation through TLR4. FIG. 26 shows protection of mouse islets against rHMGB1-mediated TLR4 inflammation with TAK-242. Islets from C57BL/6 mice were challenged with 1 μg/mL rHMGB1 with or without TAK-242 pretreatment. After 4 h, total RNA was isolated from the islets for gene expression analysis. The proinflammatory genes (A) CXCL10 and (B) CCL2 were examined in the samples. Data represented as means±SEM. *P<0.05 (n=3 for all samples, unpaired two-tailed t test).

In the results shown in FIG. 24, culture media was examined by multiplex analysis for IL-6, CXCL1, CXCL10, CCL2, and tumor-necrosis factoralpha (TNF-α). Islets treated with LPS alone showed significantly higher concentrations of the proinflammatory cytokines (FIG. 24D-24H). This is in contrast to the cytokine levels from islets that were pretreated with TAK-242 before LPS challenge, which showed significantly lower levels of these cytokines. The data demonstrate the potency of TAK-242 as a TLR4-antagonist.

Example 11—Design and Synthesis of TAK-242 Prodrug

A variety of strategies for the controlled release of covalently linked drugs have been explored. The approach used in this example for covalently attaching a TAK-242 prodrug to tissue surfaces for sustained release utilized a recently reported azide-functionalized linker and an azide/alkyne bioconjugation reaction.

FIG. 27 shows the use of cleavable prodrug chemistry, namely (A) Synthesis of TAK-PhSO2-Linker prodrug: (i) Triphosgene, pyridine, THF (ii) TAK-242, Et3N, CH2Cl2 (69% overall); (B) Synthesis of BODIPY-PhSO2-Linker: (i) Triphosgene, pyridine, THF (iii) BODIPY-TR-cadaverine, Et3N, THF (34% overall). (C) TAK-PhSO2-Linker conjugation to tissue surface and release of free TAK-242 by β-elimination.

Figure 27A:
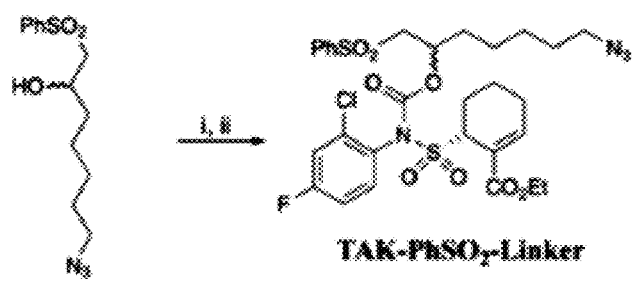
FIG. 27A shows synthesis of TAK-PhSO$_2$-Linker prodrug.
Figure 27B:
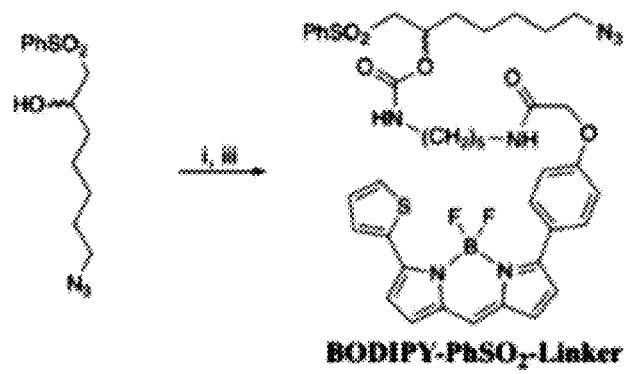
FIG. 27B shows synthesis of BODIPY-PhSO$_2$-Linker.
Figure 27C:
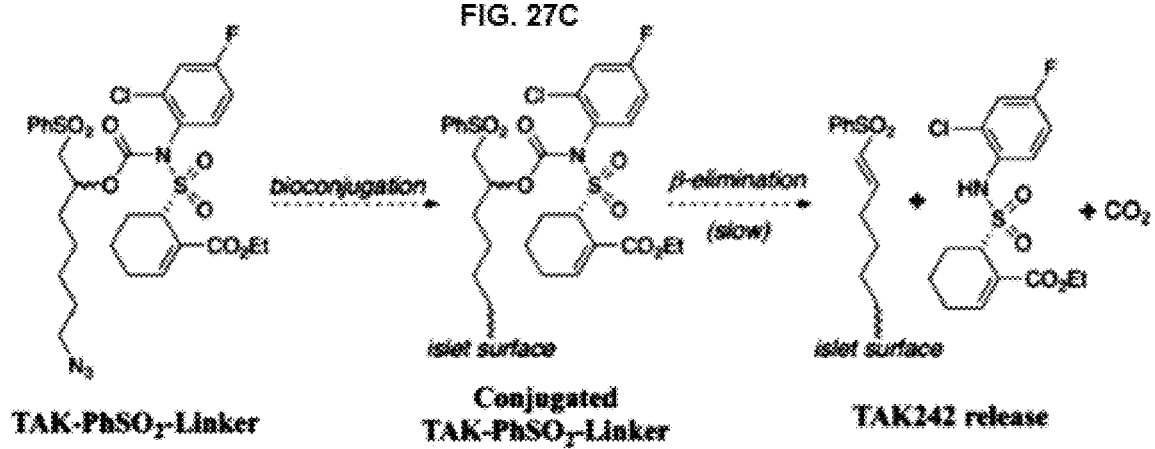
FIG. 27C shows TAK-PhSO$_2$-Linker conjugation to tissue surface and release of free TAK-242 by β-elimination.

Briefly, a linker alcohol was converted to its chlorocarbonate, which was directly reacted with the TAK-242 sulfonamide amine to afford the TAK-PhSO2-Linker prodrug in moderate yield (FIG. 27A). A fluorescent BODIPY-PhSO2-Linker compound was similarly synthesized for use in quantification studies (FIG. 27B). This linker design has been shown to hydrolytically release simple amines via a β-elimination reaction that is only modestly dependent on the basicity of the drug, independent of enzymatic cleavage mechanisms, and amenable to modulation by the selection of substituents (modulators) to adjust the pK. A phenyl sulphonyl substituted linker was selected, with a reported t1/2 of approximately three days for carbamates derived from simple aliphatic amines (pH 7.4, 37°), for these initial studies. While the nitrogen in TAK-242 is an electron poor aryl sulfonamide, N-acyl sulfonamides have been described as enzyme-stable prodrug candidates, and it was anticipated that TAK-242 would be likely released from the conjugated TAK-PhSO$_2$-Linker by β-elimination (FIG. 27C).

Detailed Synthesis of TAK-PhSO$_2$-Linker. Pyridine (27.3 μL, 0.34 mmol) was added dropwise to a stirred solution of 7-azido-1-(phenylsulfonyl)heptan-2-ol (45.5 mg, 0.15 mmol) and triphosgene (79 mg, 0.27 mmol) in 2.1 mL of anhydrous tetrahydrofuran. The resulting suspension was stirred for 20 min and filtered and concentrated to give the crude chloroformate as an oil. To the solution of the crude chloroformate in tetrahydrofuran (2.5 mL) was added ethyl 6-(N-(2-chloro-4-fluorophenyl)sulfamoyl)cyclohex-1-ene-1-carboxylate (55 mg, 0.15 mmol) and trimethylamine (38.4 μL, 0.28 mmol). The solution was stirred for 2 h at room temperature and diluted with ethyl acetate and washed with 1 M HCl, water, saturated sodium bicarbonate, and brine (5 mL each). The organic phase was dried over magnesium sulfate, concentrated, and subjected to flash chromatography using 25% ethyl acetate/hexanes. $^{13}$C NMR (126 MHz, CDCl3) δ 166.3, 166.1, 163.5, 163.5, 161.5, 161.5, 151.4, 151.3, 148.1, 146.8, 139.1, 139.0, 137.0, 136.9, 135.8, 135.7, 134.2, 134.2, 133.8, 133.0, 133.0, 132.2, 132.1, 130.6, 130.6, 129.5, 129.5, 129.5, 129.4, 128.4, 128.3, 127.5, 124.0, 123.6, 118.1, 117.9, 117.6, 117.4, 115.3, 115.1, 114.9, 114.8, 71.8, 71.8, 61.3, 61.2, 59.4, 58.7, 58.6, 58.5, 51.2, 44.6, 33.9, 33.6, 28.6, 26.2, 26.1, 25.2, 24.8, 24.0, 23.9, 23.8, 23.4, 16.8, 16.1, 14.4, 14.3; HRMS (+ESI) calculated for $C_{29}H_{34}ClFN_4NaO_8S_2$ (M+Na$^+$) 707.1383 found 707.1383 (Δ 0.0 ppm).

Detailed Synthesis of BODIPY-PhSO2-Linker. Pyridine (5.5 μL, 0.068 mmol) was added dropwise to a stirred solution of 7-azido-1-(phenylsulfonyl)heptan-2-ol (8.9 mg, 0.03 mmol) and triphosgene (17.4 mg, 0.06 mmol) in 0.4 mL of anhydrous tetrahydrofuran. The resulting suspension was stirred for 20 min and filtered and concentrated to give the crude chloroformate as an oil. To the solution of the crude chloroformate in tetrahydrofuran (2.5 mL) was added BODIPY TR Cadaverine hydrochloride 4.2 mg, 0.008 mmol) and triethylamine (2.5 μL, 0.018 mmol). The reaction was monitored by TLC (10% methanol/dichloromethane) and stirred for 2.5 h at room temperature. The solution was then diluted with ethyl acetate (10 mL) and washed with water (2×5 mL) and concentrated by the rotary evaporator. The crude material was purified by flash chromatography using 40% ethyl acetate/hexanes and then 4% to 5% methanol/dichloromethane to provide 2.2 mg of the product (34% yield). $^1$H NMR (500 MHz, CDCl3) δ 8.13-8.08 (m, 1H), 7.99-7.95 (m, 2H), 7.94-7.89 (m, 2H), 7.66-7.62 (m, 1H), 7.57-7.52 (m, 2H), 7.47 (d, J=6.0 Hz, 1H), 7.19 (s, 1H), 7.16-7.13 (m, 1H), 7.08 (dd, J=12.2, 4.3 Hz, 2H), 7.04-6.99 (m, 2H), 6.82 (d, J=4.3 Hz, 1H), 6.66 (d, J=4.4 Hz, 1H), 5.12-5.05 (m, 1H), 4.56 (s, 2H), 4.44 (t, J=6.0 Hz, 1H), 3.45-3.34 (m, 3H), 3.22 (t, J=6.8 Hz, 2H), 3.05 (q, J=6.8 Hz, 2H), 1.41-1.57 (m, 8H), 1.23-1.37 (m, 8H); HRMS (+ESI) calculated for $C_{40}H_{44}BF_2N_7NaO_6S_2^+$ (M+Na$^+$) 854.2748 found 854.2737.

Example 12—Islet Modification

Figure 28A:
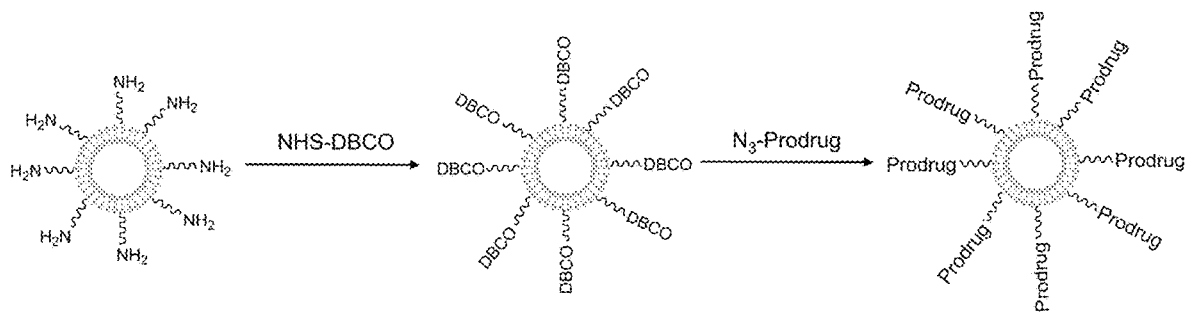
FIG. 28A shows a representative scheme of functionalizing tissue surfaces.

Murine, porcine, and human islets are amenable to surface modifications using several bioorthogonal conjugation chemistries. The chemistry used in the present example to functionalize tissue surfaces, depicted in FIG. 28A, involves a two-step process that harnesses the biocompatibility and modularity of copper-free click chemistry. FIG. 28A shows a scheme of functionalizing tissue surfaces using SPAAC. NHS-PEG4-DBCO can be used to attach reactive alkynes (DBCO) by the reaction of N-hydroxysuccinimide (NHS) esters with primary amines on the tissue surface. This allows an azide-substituted prodrug to be covalently linked to the tissue surface via azide-alkyne cycloaddition reaction.

A commercially available bifunctional linker, the dibenzocyclooctyne-PEG4-Nhydroxysuccinimidiyl ester (NHS-PEG4-DBCO), was initially used to label reactive amines on surface of the islets with a strained alkyne, which were then reacted with the linker compounds via strain-promoted azide-alkyne cycloaddition (SPAAC). Specifically, isolated islets from culture were rinsed once with Krebs-Ringer Bicarbonate Buffer (KRBH; pH 7.4) (Sigma-Aldrich) and then incubated with 25 μM NHS-PEG4-DBCO (Sigma-Aldrich) in KRBH (pH 7.7) for 1 h at room temperature. Islets were rinsed once with KRBH (pH 7.4) to remove unreacted NHS-PEG4-DBCO and then subsequently reacted with TAK-PhO2-Linker (10-25 μM) or BODIPY-Linker (10 μM) for 1 h at room temperature. Islets were then washed twice with KRBH (pH 7.4) to generate TAK-PhO$_2$-Linker or BODIPY-Linker modified islets. Modified islets were cultured or used immediately for experiments.

Figure 28B:
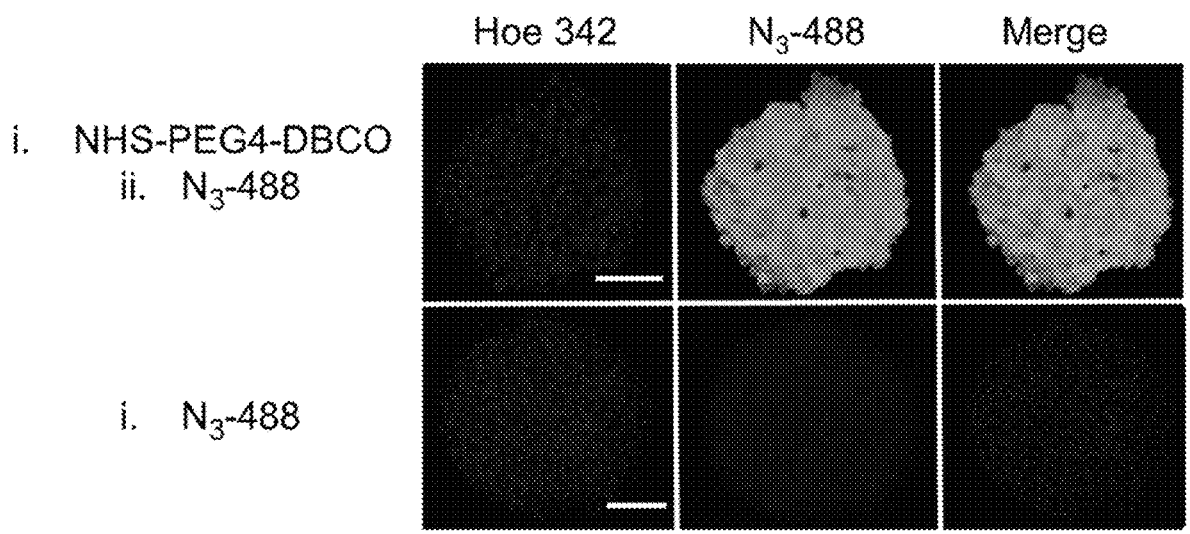
FIG. 28B shows representative fluorescent images of a surface-functionalized islet successfully labeled with a fluorescent dye compared to an islet that was not surface functionalized.

To confirm the initial acylation reaction, islets were treated with NHS-PEG4-DBCO followed by carboxyrhodamine-110 azide (N3-488) and observed significant surface labeling, while islets treated with N3-488 alone showed no labeling (FIG. 28B). FIG. 28B shows fluorescent images of a surface-functionalized islet successfully labeled with a fluorescent dye via SPAAC compared to an islet that was not surface functionalized with NHS-PEG4-DBCO before staining with N3-488. Nuclei were stained with Hoechst 33342.

Figure 28C:
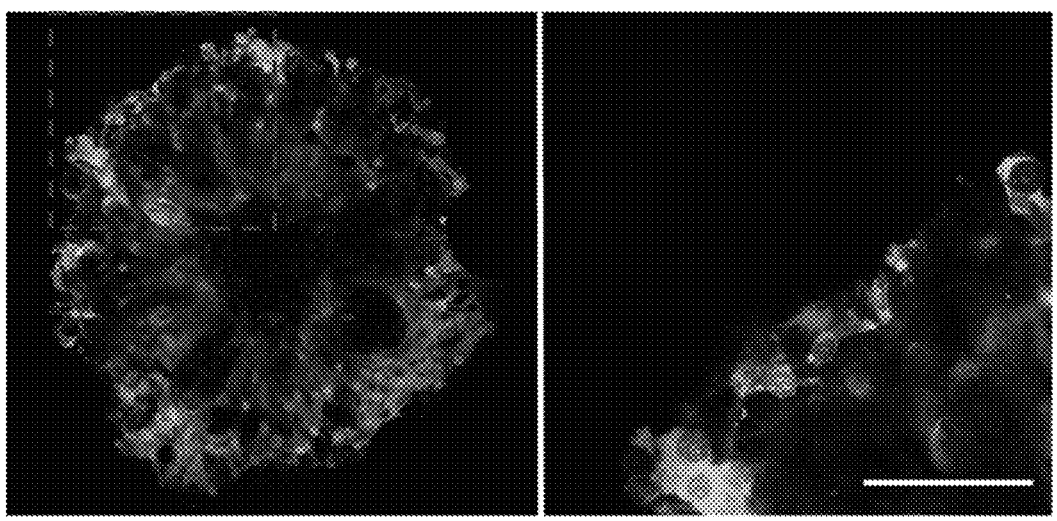
FIG. 28C shows a confocal image of fluorescently modified islets showing the modification on the surface of the islets.
Figure 28D:
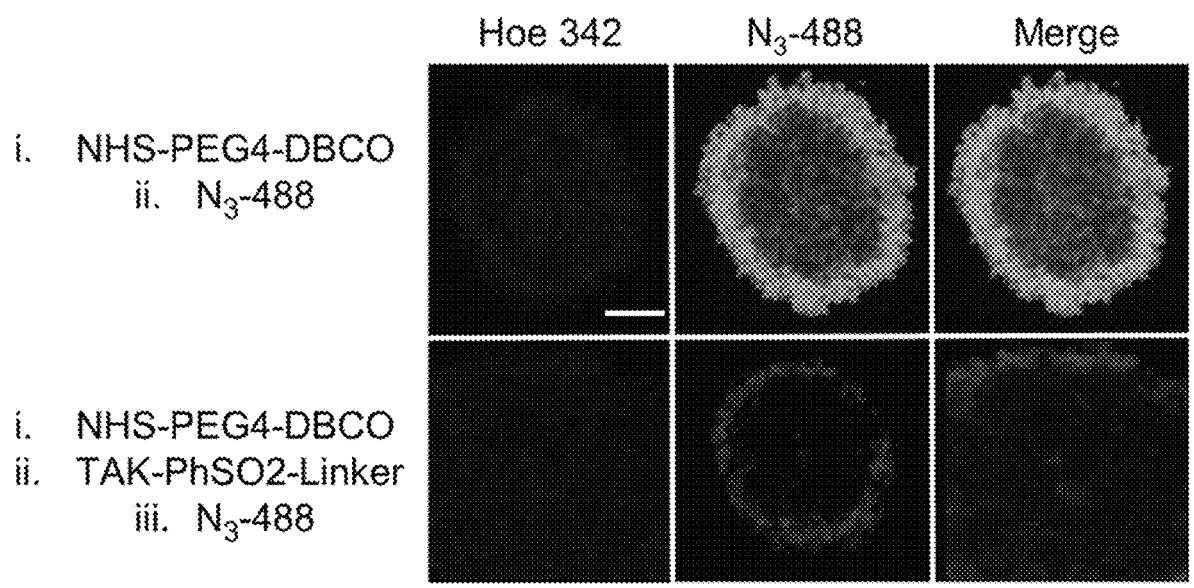
FIG. 28D shows representative fluorescent images of alkyne-functionalized islets.
Figure 28E:
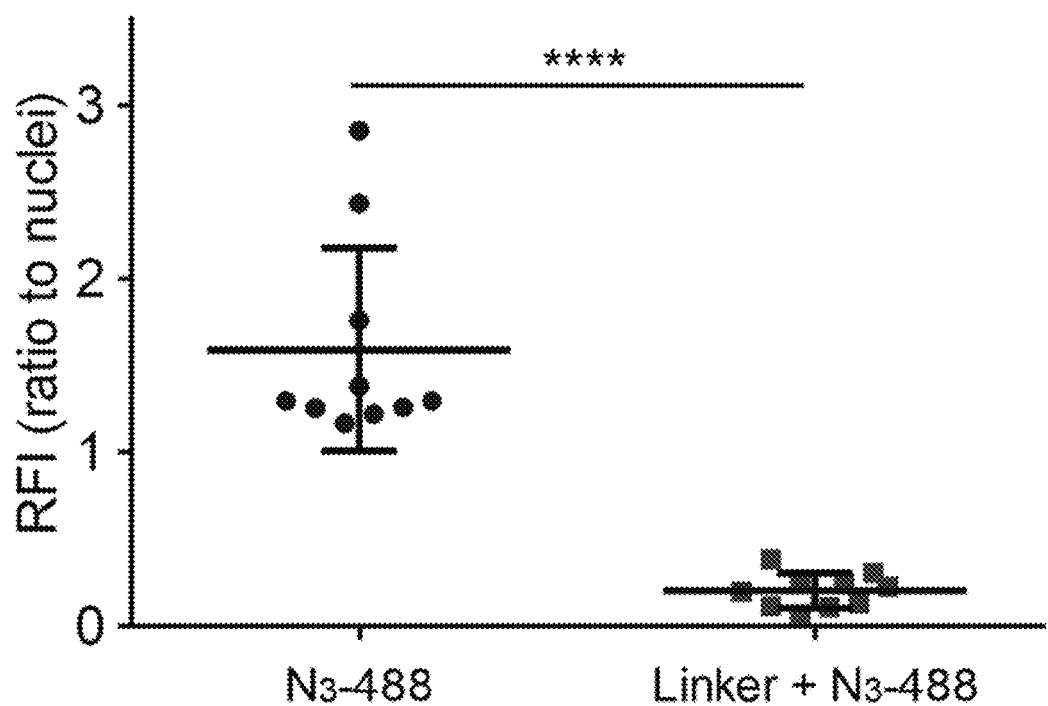
FIG. 28E shows quantification of fluorescent modification from both groups normalized to nuclei staining.

Confocal microscopy was used to confirm that the reactions occurred on the islet surface (FIG. 28C). FIG. 28C shows a representative confocal image of fluorescently modified islets showing the modification on the surface of the islets. Next, a competitive binding model was used to demonstrate that the compound, TAK-PhSO$_2$-Linker, reacted with alkyne-functionalized islet surfaces. In this experiment, it was observed that incubating surface-functionalized islets with the TAK-PhSO$_2$-Linker prior to treatment with N3-488 significantly reduced the fluorescent labeling (P<0.0001; FIG. 28D-28E), demonstrating that the TAK-242 prodrug compounds successfully reacted with islet surface alkynes. FIG. 28D shows representative fluorescent images of alkyne-functionalized islets reacting with N3-488 alone or with TAK-PhSO$_2$-Linker followed with N3-488. FIG. 28E shows quantification of fluorescent modification from both groups normalized to nuclei staining. Data are represented as means±SD (n=10 per group, ****P<0.0001 two-tailed unpaired t test).

It was also demonstrated that murine kidneys are also amenable to this conjugation chemistry, suggesting that the drug-eluting live tissue concept should be readily translatable to different organs and tissue types. Kidneys from nude mice were cannulated through the renal artery and perfused with Hoechst 33342 and N3-488 alone or NHS-PEG4-DBCO plus N3-488. After perfusion, kidneys were resected and embedded in optimal cutting temperature compound. Frozen sections were prepared and mounted on slides for fluorescent microscope imaging. While the kidney perfused with N3-488 alone showed only background fluorescence, the kidney functionalized with NHS-PEG4-DBCO displayed significant labeling with N3-488.

Example 13—Drug Load And Release Kinetics

Figure 29A:
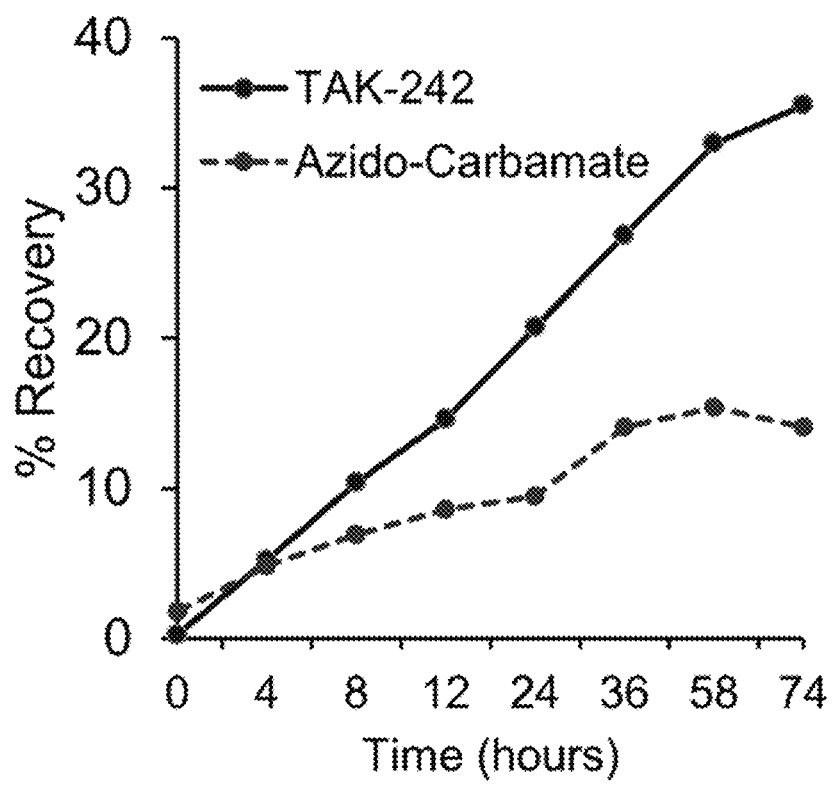
FIG. 29A shows conversion of TAK-PhSO$_2$-Linker into TAK-242 or the azido-carbamate side product.
Figure 29B:
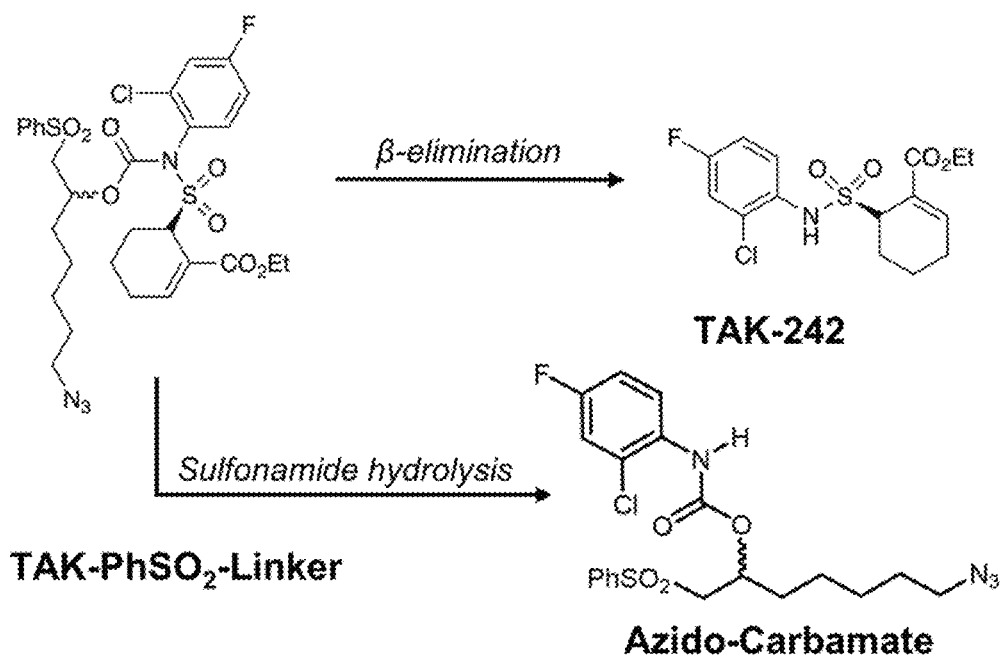
FIG. 29B shows TAK-PhSO$_2$-Linker hydrolysis products.

The stability of the linker prodrug was explored in this example. The TAK-PhSO$_2$-Linker compound was incubated in phosphate-buffered saline (PBS; pH 7.4) at 37° C., and the solution sampled over the course of several days. Liquid chromatography-mass spectrometry (LC-MS) was used to identify and quantitate the compounds released from this prodrug. This experiment revealed that the half-life of TAK-PhSO$_2$-Linker was ~25 h, and that a second compound resulting from sulfonamide hydrolysis was also formed under these conditions (FIG. 29A-29B). FIG. 29A shows conversion of TAK-PhSO$_2$-Linker into TAK-242 or the azido-carbamate side product. FIG. 29B shows TAK-PhSO$_2$-Linker hydrolysis products. The observed half-life of TAK-PhSO$_2$-Linker was shorter than what has been previously reported for this linker attached to primary amines, likely due to the significantly enhanced acidity of the sulfonamide amine.

Figure 29C:
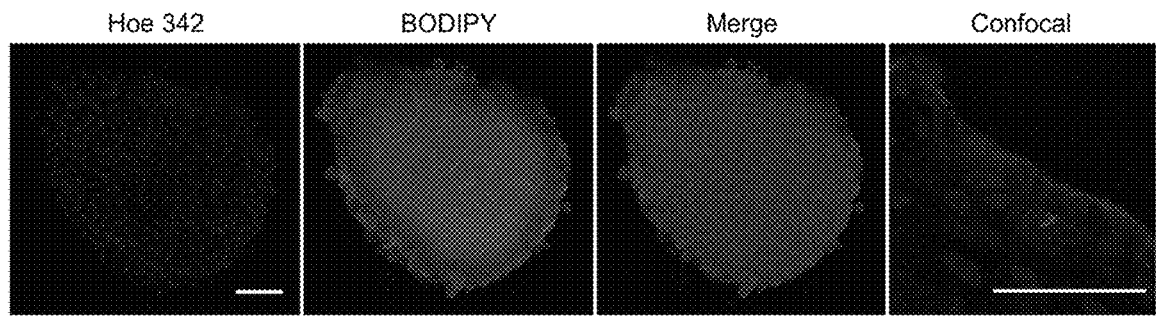
FIG. 29C shows a fluorescent image of a representative islet modified with BODIPY-PhSO$_2$-Linker.
Figure 29D:
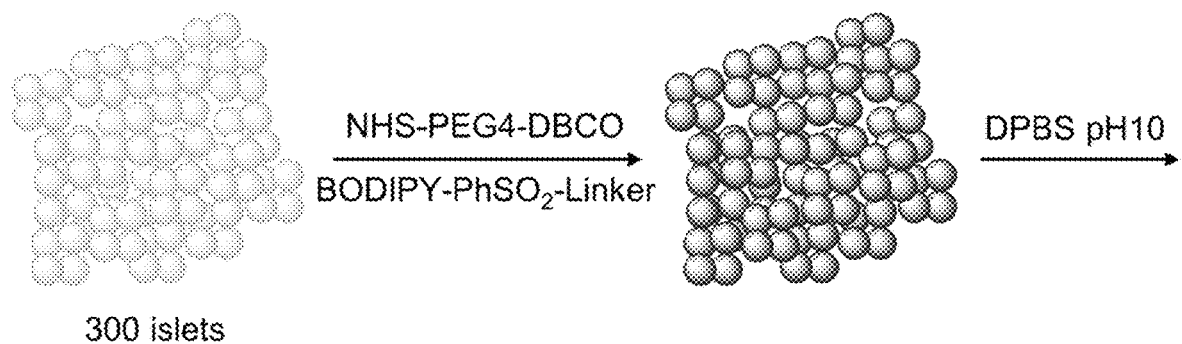
FIG. 29D shows experimental design of islet drug-loading capacity.
Figure 29E:
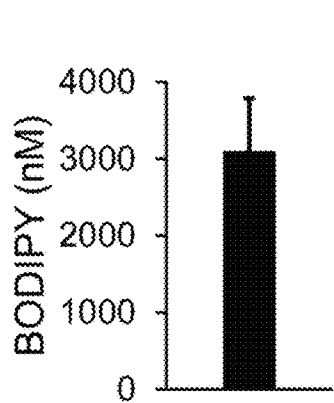
FIG. 29E shows quantification of islet drug-loading capacity.
Figure 29F:
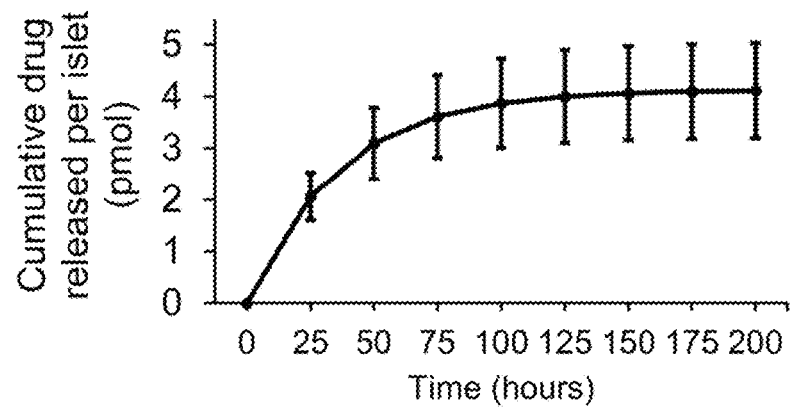
FIG. 29F shows theoretical cumulative release of TAK-242 over time.

The potential drug dose delivered is another important parameter, and so the effective islet drug-loading capacity of this DBCO/azide-linker chemistry was measured. This was accomplished by modifying islets with NHS-PEG4-DBCO followed by our fluorophore/linker molecule (BODIPY-PhSO$_2$-Linker) (FIG. 29C). FIG. 29C shows a fluorescent image of a representative islet modified with BODIPY-PhSO$_2$-Linker. FIGS. 29D and 29E show experimental design and quantification of islet drug-loading capacity. FIG. 29F shows theoretical cumulative release of TAK-242 over time. Data represented as means±SD.

Figure 30:
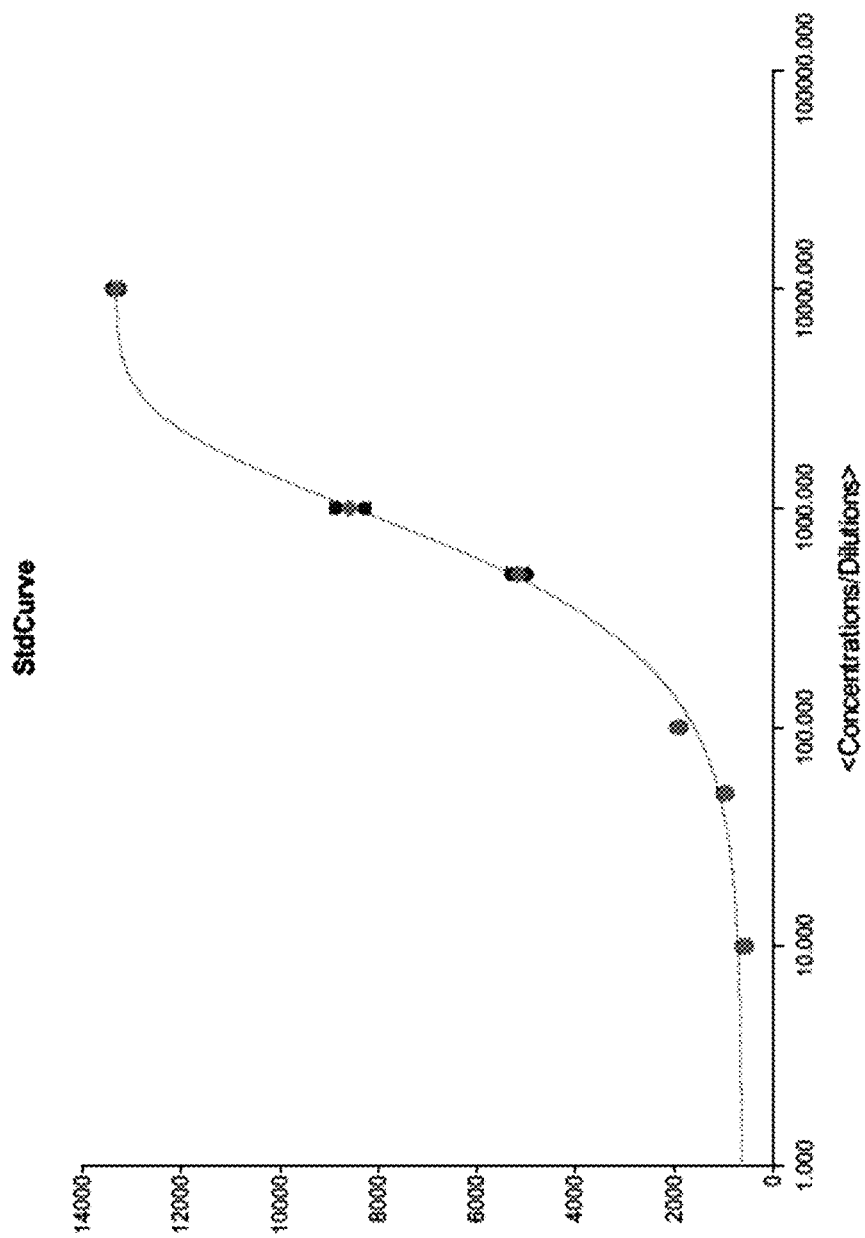
FIG. 30 shows a standard curve for BODIPY-TR quantification.

The hydrolysable linkage on the resulting islets were rapidly cleaved in a pH 10 cleavage buffer, and the released dye was quantified by plotting the relative fluorescent intensity of the cleavage buffer against a standard curve. FIG. 30 shows a standard curve for BODIPY-TR quantification.

From 300 modified islets, a BODIPY concentration of 3101.57±690.73 nM in 400 μL of cleavage buffer was measured (FIG. 29E). The equates to approximately 1.24±0.276 nmol of compound released, or 4.13±0.92 pmol of compound per islet. Since the effective concentrations (IC50) of 1 (TAK-242) as a TLR4 antagonist are in the low nanomolar range (1-33 nM depending on cell type), this suggests the capacity for the release of biologically relevant amounts of the active drug. For example, the release of 0.03 pmol (<1% of the bound drug per islet) distributed into a volume of ~1 microliter (volume of >1000 islets) provides a dose of 30 μM, or greater than 1000× the IC50. The theoretical cumulative compound release over time is depicted in FIG. 29F.

Example 14—Viability and Functionality of Modified Islets

The viability of islets was assessed after covalent modification by staining islets with Hoechst 33342 and propidium iodide (PI) at various time points to ensure that the islet manipulations, reactive compounds, and modification reactions did not induce toxicity. Islets isolated from C57BL/6 mice were modified with NHS-PEG4-DBCO followed by TAK-PhSO$_2$-Linker and cultured for up to 5 days. The viability of unmodified and modified islets (n=10 per group) was evaluated on days 1, 2, and 5 post-modification by calculating the ratio of PI-positive cells to Hoechst 33342-positive cells (FIG. 32A).

FIG. 31 shows the results of modified islet viability and functionality assays. FIG. 31A shows viability of control and modified islets assessed by Hoechst 33342 and PI staining on days 1, 2, and 5 postmodification. Data are represented as means±SEM (n=10 per group, P=0.13, two-tailed unpaired t test). FIGS. 31B and 31C show stimulation index of control and modified islets 24 h and 72 h postmodification. Data are represented as means±SD (n=2 per group; P=0.22 and 0.44, respectively). FIG. 31D shows intracellular Ca$^{2+}$ flux assessment by fura-2AM staining (n=1 per group). Arrow indicates an injection of 20 mM glucose. AUC is quantified in the inset graph. n.s. means not significant.

No significant difference in mean viability was observed between unmodified and modified islets at any time points (P=0.13), which is consistent with published data on SPAAC modifications in living systems and on covalent islet modification. The modification of islets with NHS-PEG4-DBCO/TAK-PhSO$_2$-Linker also had no significant effects on islet function. Glucose-stimulated insulin secretion assays were performed on unmodified and modified islets, and no differences were detected in the stimulation index between unmodified and modified islets at day 1 (P=0.22; FIG. 31B) or at day 3 (P=0.44; FIG. 31C). Intracellular Ca$^{2+}$ flux in response to high glucose also remained identical in modified islets (FIG. 31D). These experiments demonstrate that islets tolerate this covalent surface modification.

Example 15—Protection of Drug-Eluting Islets In Vitro

In order to study the function and efficacy of the cleavable prodrug, in vitro experiments were performed challenging mouse islets with LPS at different times post-modification. First, it was demonstrated that although TAK-242 is a potent TLR4 antagonist, the intact prodrug construct (TAK-PhSO$_2$-Linker) has negligible TLR4-antagonist activity. HEK Blue hTLR4 reporter cells were treated with either free TAK-242 or the TAK-PhSO$_2$-Linker prodrug, followed by LPS challenge.

FIG. 32 shows the results of an assessment of drug-eluting islet protection in vitro. FIG. 32A shows assessment of inhibition of TLR4-mediated NFkB upregulation for free TAK-242 and the TAK-PhSO$_2$-Linker prodrug using a colorimetric assay. TAK-242 completely blocked LPS while the intact prodrug provided no protection. FIG. 32B shows that islets covalently modified with TAK-PhSO$_2$-Linker were significantly protected from LPS challenge (P<0.001) as determined by IL-6 expression. FIG. 32C shows protection of modified islets explored out to 48 h postmodification. At both 24 and 48 h after modification, covalently modified islets were protected against LPS as well as islets treated with TAK-242 30 minutes prior to challenge. FIG. 32D shows that both free TAK-242 and the covalent TAK-PhSO$_2$-Linker modification provided protection from TLR4-mediated inflammation 24 hours post treatment, but the protection provided by the surface modification was significantly better than that of free TAK-242 alone. FIG. 32E shows that islet surfaces functionalized with NHS-PEG4-DBCO demonstrated no protection against LPS-mediated inflammation (P=0.60). Data represented as means±SEM (n=3 per group). Statistical significance determined by two-tailed unpaired t test. n.s. means not significant.

While brief treatment with free TAK-242 completely inhibited the upregulation of NFkB after LPS challenge, no significant protection was provided by brief treatment with the unconjugated TAK-PhSO$_2$-Linker (FIG. 32A). When conjugated to islets, TAK-PhSO$_2$-Linker significantly protected against LPS-mediated inflammation 24 h after modification (P<0.0001; FIG. 32B). It was also observed that the prodrug modified islets provided potent protection, comparable to TAK-242 treatment 30 min prior and greatly superior to TAK-242 24 h prior (P<0.05), that continued for at least 48 h postmodification (FIG. 32C-32D). Not surprisingly, simple covalent surface modification lacking the prodrug functionality did not reduce the LPS-mediated IL-6 upregulation (P=0.60; FIG. 32E). These results demonstrate that the cleavable TLR4-antagonist prodrug is functional and when covalently attached to islet surfaces provides potent and durable protection against TLR4-mediated inflammation in vitro.

Example 16—Efficacy of Drug-Eluting Islets in Islet Transplant Model

With the promising in vitro results described above, islet transplantation experiments were performed in a syngeneic wild-type C57BL/6 streptozotocin-induced diabetes model. Recipient male C57BL/6 mice 6-7 weeks old were made diabetic by a single intraperitoneal injection of streptozotocin (200 mg/kg; Sigma-Aldrich). Diabetic mice are defined as having a nonfasting blood glucose >400 mg/dL for 2 consecutive days. Prior to transplantation, islets were untreated, pretreated with 3 μM TAK-242, or modified with TAK-PhSO$_2$-Linker as described above. Diabetic C57BL/6 mice were anesthetized under isoflurane, and a field between the rib cage and pelvis on the left side was disinfected by 1% providone iodine scrub and 70% ethanol. A minimal incision (~8 to 10 mm) into the peritoneum was made to expose the kidney, and a small cut (~2 mm) was made in the kidney capsule using a 30G needle. Then a flame-blunted glass pipette tip was inserted into the kidney capsule through the cut to create a pocket between the renal cortex and capsule. Islets were then injected into the pocket via PE-50 polyethylene tubing (Becton Dickinson) connected to a 1 mL syringe filled with RPMI 1640 driven by an NE-300 syringe pump (New Era Pump Systems). At the completion of islet infusion, the incision was closed with 4-0 violet monofilament (Ethicon) via continuous nonlocking sutures. After closing, mice received a 0.1 mg/kg bolus of buprenorphine subcutaneously near the incision. Engraftment success was measured by nonfasting blood glucose measurements 5 times a week over a 4-week period with a Breeze 2 Glucose Monitor (Bayer). Mice were considered cured on the first day of two consecutive glucose measurements below 200 mg/dL (~11 mM).

Figure 33A:
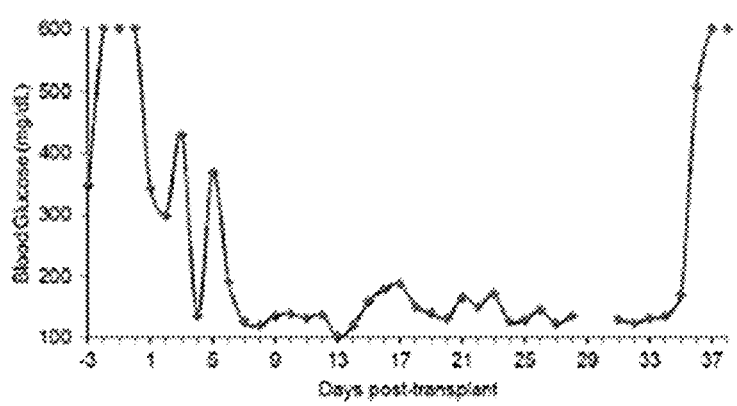
FIG. 33A shows blood glucose over time following islet dose titration with 200 islets pretreated with TAK-242.
Figure 33B:
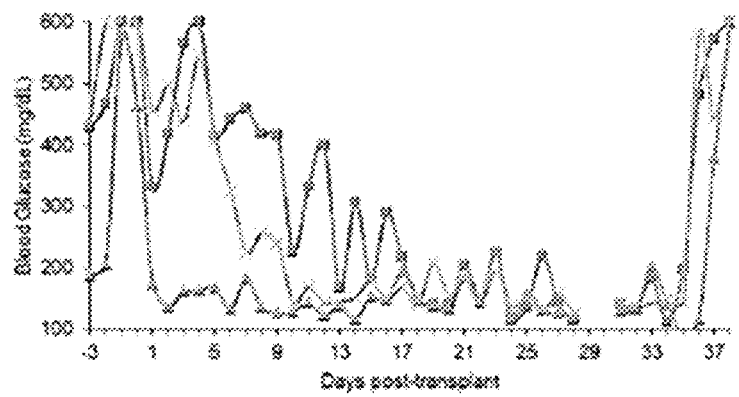
FIG. 33B shows blood glucose over time following islet dose titration with 150 islets pretreated with TAK-242.
Figure 33C:
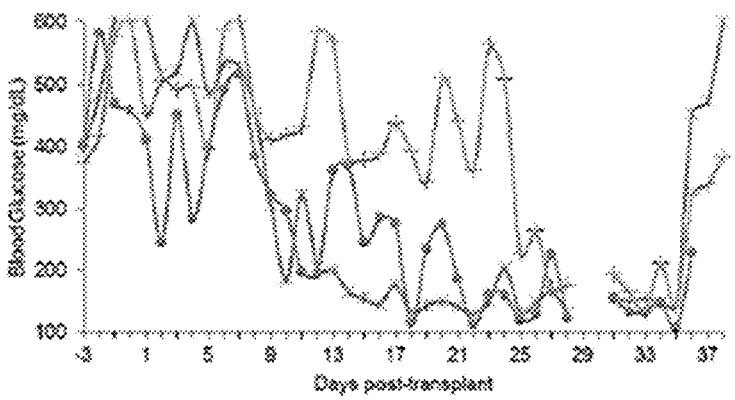
FIG. 33C shows blood glucose over time following islet dose titration with 100 islets pretreated with TAK-242.

Diabetic mice were separated into untreated (n=4), TAK-242 (n=6), and TAK-PhO$_2$-Linker (n=6) groups. A marginal dose of ~100 islets was determined by titrating doses of TAK-242-treated islets. FIG. 33 shows islet dose titration with TAK-242 pretreated islets. Diabetic C57BL/6 mice were transplanted with (FIG. 33A) 200, (FIG. 33B) 150, or (FIG. 33C) 100 TAK-242-treated islets. Blood glucose was monitored for 4 weeks before IPGTT on day 30 and at nephrectomy on day 35. The quantity of 200 and 150 islets showed quick cure times and good glycemic control; the quantity of 100 islets had a delayed cure time and exhibited significant average glycemic lability. This marginal dose was transplanted into the kidney subcapsular space in each group, and blood glucose was monitored for 4 weeks.

FIG. 34 shows the results for islet transplant outcomes and function in a syngeneic model. FIG. 34A shows mean nonfasting blood glucose in control (n=4), TAK-242 (n=6), and modified (n=6) groups. Mice receiving 100 untreated islets (Control) did not demonstrate any blood glucose control, while mice receiving 100 TAK-242-treated and modified islets demonstrated some control. Only the group receiving modified islets achieved a mean blood glucose concentration in the normoglycemic range (<200 mg/dL). FIG. 34B shows that all (6/6) mice receiving 100 modified islets achieved euglycemia (P=0.004) compared to 67% (4/6) of mice receiving 100 TAK-242-treated islets (P=0.052). No mice in the control group achieved euglycemia. FIG. 34C shows a dissecting microscopic image of a neovascularized islet graft from a mouse that received 100 modified islets. FIGS. 34D and 34E show IPGTT data from mice on day 30 posttransplant. AUC analysis showed no difference between the control and TAK-242 group (P>0.05), but a significant difference between the modified group and both the control and TAK-242 group (*P<0.05, one-way ANOVA with Newman-Keuls multiple comparisons test). Data represented as means±SEM. n.s. means not significant.

All mice receiving modified islets became euglycemic with a mean time to cure of 17.2±6.3 days (FIG. 34B), and 67% of mice receiving islets treated with free TAK-242 became euglycemic at 21.0±4.9 days (FIG. 34A-34B). None of the mice in the control group achieved euglycemia during the monitoring period (FIG. 34B). The cure rate of the mice implanted with prodrug modified islets was significantly superior to those transplanted with free TAK-242-treated islets (P=0.004 and 0.052, respectively, log-rank). Visual analysis of the modified islet grafts showed preservation of the islet mass and significant vascularization in the euglycemic mice (FIG. 34C), suggesting the treatment does not impair revascularization of islets posttransplant.

An intraperitoneal glucose tolerance test (IPGTT) was performed at day 30 posttransplant to assess graft function. IPGTT area under the curve (AUC) analysis showed that the mice receiving the modified islets had the most robust glucose clearance response (FIGS. 34D-34E). Islet grafts were removed by nephrectomy of the transplanted kidney to demonstrate that the mice became cured due to the grafts and not because of regeneration of endogenous insulin, and a prompt return to a diabetic state was observed in previously cured animals.

FIG. 35 shows blood glucose of mice after islet graft removal by nephrectomy. Nephrectomy of the islet-transplanted kidney was performed on day 35 posttransplant. FIG. 35A shows control mice remained diabetic. FIGS. 35B and 35C show cured mice in the TAK-242 group and modified group quickly returned to a diabetic state.

These data demonstrate that drug-eluting modified islets significantly reduce the time and islet dose required for achieving euglycemia in diabetic mice.

What is claimed is:

1. A method for producing a modified protected transplant tissue, comprising:
   obtaining live tissue intended for transplant into a recipient;
   contacting the surface of the live tissue with a functionalizing compound to create reactive surface moieties on the surface of the live tissue and produce a reactive tissue surface;
   contacting the reactive tissue surface with a therapeutic-linker compound, wherein the therapeutic-linker compound comprises a therapeutic agent and a releasable linker moiety, wherein the releasable linker moiety comprises a carbamate released by β-elimination, whereby the reactive surface moieties of the reactive tissue surface react with the releasable linker moiety of the therapeutic-linker compound to link the therapeutic-linker compound to the reactive tissue surface by the releasable linker moiety and produce modified protected tissue;
   transplanting the modified protected tissue into a transplant site of a recipient;
   cleaving the releasable linker moiety in vivo in the recipient, wherein the releasable linker moiety is cleaved in vivo due to chemical reactions at the transplant site; and
   releasing the therapeutic agent in a localized manner and at a tailored release rate at the transplant site of the recipient to produce extended anti-inflammatory or immunosuppressive effects on the modified protected tissue, to produce a modified protected transplant tissue, wherein the tailored release rate is based on kinetics of the chemical reactions at the transplant site wherein the therapeutic agent is TAK-242.

2. The method of claim 1, wherein the live tissue comprises pancreatic islets.

3. The method of claim 1, wherein the functionalizing compound comprises a bi-functional NHS-Alkyne compound.

4. The method of claim 1, wherein the functionalizing compound comprises dibenzocyclooctyne-PEG4-N-hydroxysuccinimidyl ester (NHS-PEG4-DBCO).

5. The method of claim 1, wherein the therapeutic-linker compound has the structure:

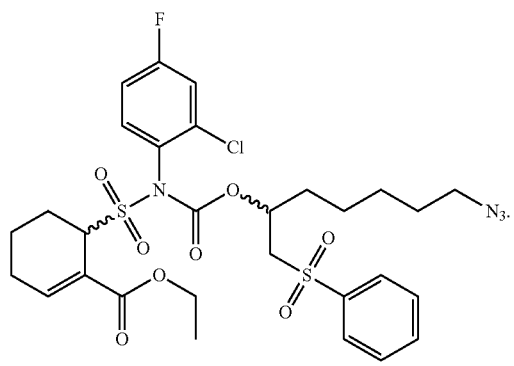 [SMILES: CCOC(=O)C1=CCCCC1S(=O)(=O)N(C(=O)OC(CCCCCN=[N+]=[N-])CS(=O)(=O)c1ccccc1)c1ccc(F)cc1Cl]

6. The modified protected transplant tissue prepared by the method of claim 1.

7. A method for modifying a surface of pancreatic islets with a protective therapeutic agent to produce modified protected islets and improve transplantation success, comprising:
   obtaining live pancreatic islets intended for transplant into a recipient;
   contacting the surface of the live pancreatic islets with a functionalizing compound to create reactive surface moieties on the surface of the live pancreatic islets and produce a reactive tissue surface;
   contacting the reactive tissue surface with a therapeutic-linker compound, wherein the therapeutic-linker compound comprises TAK-242 and a releasable linker moiety, wherein the releasable linker moiety comprises a carbamate released by β-elimination, whereby the reactive surface moieties of the reactive tissue surface react with the releasable linker moiety of the therapeutic-linker compound to link the therapeutic-linker compound to the reactive tissue surface by the releasable linker moiety and produce modified protected islets;
   transplanting the modified protected islets into a transplant site of a recipient;
   cleaving the releasable linker moiety in vivo in the recipient, wherein the releasable linker moiety is cleaved in vivo due to chemical reactions at the transplant site; and
   releasing the TAK-242 is released in a localized manner and at a tailored release rate at the transplant site of the recipient to produce extended anti-inflammatory or immunosuppressive effects on the modified protected islets, to produce modified protected transplanted islets, wherein the tailored release rate is based on kinetics of the chemical reactions at the transplant site.

8. The method of claim 7, wherein the functionalizing compound comprises dibenzocyclooctyne-PEG4-N-hydroxysuccinimidyl ester (NHS-PEG4-DBCO).

9. The method of claim 7, wherein the therapeutic-linker compound has the structure:

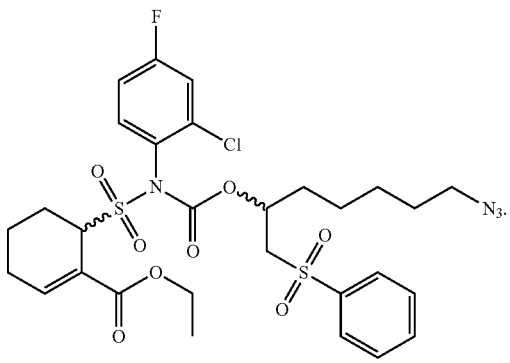 [SMILES: CCOC(=O)C1=CCCCC1S(=O)(=O)N(C(=O)OC(CCCCCN=[N+]=[N-])CS(=O)(=O)c1ccccc1)c1ccc(F)cc1Cl]

10. A therapeutic-linker compound for use in modifying the surface of live tissue intended for transplant to improve transplantation success having the structure:

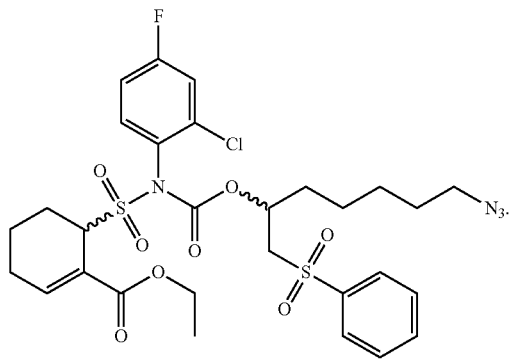 [SMILES: CCOC(=O)C1=CCCCC1S(=O)(=O)N(C(=O)OC(CCCCCN=[N+]=[N-])CS(=O)(=O)c1ccccc1)c1ccc(F)cc1Cl]

11. A method for modifying a surface of pancreatic islets with a protective therapeutic agent to produce modified protected islets and improve transplantation success, comprising:
   obtaining live pancreatic islets intended for transplant into a recipient;
   contacting the surface of the live pancreatic islets with dibenzocyclooctyne-PEG4-N-hydroxysuccinimidyl ester (NHS-PEG4-DBCO) to create reactive surface moieties on the surface of the live pancreatic islets and produce a reactive tissue surface;
   contacting the reactive tissue surface with a therapeutic-linker compound, wherein the therapeutic-linker compound comprises TAK-242 and a releasable linker moiety, and wherein the therapeutic-linker compound has the structure

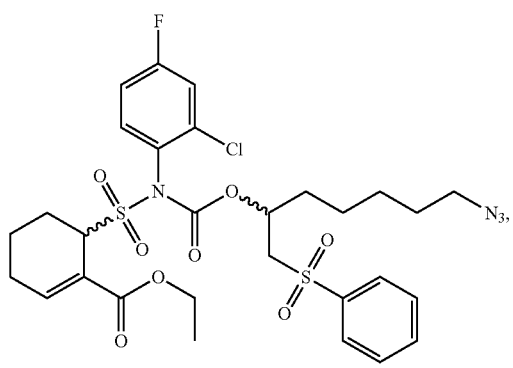 [SMILES: CCOC(=O)C1=CCCCC1S(=O)(=O)N(C(=O)OC(CCCCCN=[N+]=[N-])CS(=O)(=O)c1ccccc1)c1ccc(F)cc1Cl]

whereby the reactive surface moieties of the reactive tissue surface react with the therapeutic-linker compound to link the therapeutic-linker compound to the reactive tissue surface by a releasable linker moiety and produce modified protected islets; and
   transplanting the modified protected islets into a transplant site of a recipient, whereby the releasable linker moiety is cleaved in vivo in the recipient and the TAK-242 is released in a localized manner at the transplant site of the recipient.

* * * * *